(12) United States Patent
Jedlitschky et al.

(10) Patent No.: US 6,235,785 B1
(45) Date of Patent: May 22, 2001

(54) METHODS FOR IDENTIFYING AND TREATING RESISTANT TUMORS

(75) Inventors: Gabriele Jedlitschky; Inka Leier, both of Bammental; Dietrich Keppler, Dossenheim, all of (DE)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/793,659

(22) PCT Filed: Aug. 31, 1995

(86) PCT No.: PCT/US95/11125

§ 371 Date: Feb. 26, 1997

§ 102(e) Date: Feb. 26, 1997

(87) PCT Pub. No.: WO96/06604

PCT Pub. Date: Mar. 7, 1996

Related U.S. Application Data

(63) Continuation-in-part of application No. 08/298,644, filed on Aug. 31, 1994, now Pat. No. 5,543,428.

(30) Foreign Application Priority Data

Sep. 13, 1994 (DE) ................................ 44 32 563

(51) Int. Cl.$^7$ .................................................. A61K 31/19
(52) U.S. Cl. ............................................................ 514/568
(58) Field of Search ............................................. 514/568

(56) References Cited

U.S. PATENT DOCUMENTS

| | | |
|---|---|---|
| 4,200,577 | 4/1980 | Buckle et al. .................. 424/281 |
| 4,211,791 | 7/1980 | Buckle et al. .................. 424/304 |
| 4,889,871 | 12/1989 | Djuric et al. ................... 514/456 |
| 5,216,024 | 6/1993 | Markaverich et al. ........... 514/543 |
| 5,216,172 | 6/1993 | Toyota et al. .................. 546/321 |
| 5,302,727 | 4/1994 | Eliason et al. ................... 549/22 |
| 5,324,743 | 6/1994 | Dillard et al. .................. 514/456 |
| 5,387,685 | 2/1995 | Powell et al. .................. 546/143 |
| 5,462,954 | 10/1995 | Baker et al. .................... 514/381 |
| 5,543,428 | 8/1996 | Sawyer et al. ................. 514/456 |

FOREIGN PATENT DOCUMENTS

| | | |
|---|---|---|
| 0 292 977 A1 | 11/1988 | (EP) . |
| 0 544 488 | 6/1993 | (EP) . |
| 0 596 725 A2 | 5/1994 | (EP) . |
| 0 652 004 A1 | 5/1995 | (EP) . |
| WO 93/15733 | 8/1993 | (WO) . |
| WO 93/16044 | 8/1993 | (WO) . |
| WO 94/06938 | 3/1994 | (WO) . |
| WO 94/24107 | 10/1994 | (WO) . |

OTHER PUBLICATIONS

"Preparation of (acylamino)benzoic acid derivatives as reverse transcriptase inhibitors", Fukushima,, Okuyama and Miyamoto, Chemical Abstracts, vol. 114(9), Abstract No. 81260g, Mar. 4, 1991, p. 677.

"Profiling of Inhibitors of Protein Kinase C", Wennogle, Halyna and Jeng, Advances in Enzyme Regulation, vol. 27, 1988, pp. 287–293.

"Multiple Actions of the Leukotriene $B_4$ Receptor Antagonist SC–41930", Villani–Price, Yang, Walsh, Fretland, Keith, Kocan, Kachur, Gaginella and Tsai, The Journal of Pharmacology and Experimental Therapeutics, vol. 260(1), Jan., 1992, pp. 187–191.

"Energy–dependent export of leukotriene $B_4$ in *Xenopus oocytes*", Mori, Izumi and Shimizu, Biochimica et Biophysica Acta, vol. 1168(1), 1993, pp. 23–29.

"SC–41930, a leukotriene $B_4$ receptor antagonist, inhibits 12(S)–hydroxyeicosatetraenoic acid (12(S)–HETE) binding to epidermal cells", Kemeny and Ruzicka, Agents and Actions, vol. 32(3/4), Mar. 1991, pp. 339–342.

"Characterization of the ATP–dependent leukotriene $C_4$ export carrier in mastocytoma cells", Leier, Jedlitschky, Buchholz and Keppler, Eur. J. Biochem, vol. 220 (2), 1994, pp. 599–606.

"ATP–dependent leukotriene export from mastocytoma cells", Schaub, Ishikawa and Keppler, Febs Letters, vol. 279(1), Feb. 1991, pp. 83–86.

"The MRP Gene Encodes and ATP–dependent Export Pump for Leukotrience $C_4$ and Structurally Related Conjugates", Leier, Jedlitschky, Buchholz, Cole, Deeley and Keppler, The Journal of Biological Chemistry, vol. 269(45), Nov. 11, 1994, pp. 27807–27810.

"ATP–dependent glutathione conjugate transport in HL60 cells overexpressing the multidrug resistance associated protein (MRP)", Jedlitschky, Leier, Buchholz, Barnouin, Center and Keppler, Anticancer Drugs, vol. 5(Suppl. 1), Sep. 1994, p. 4.

"Transport of Glutathione, Glucuronate, and Sulfate Conjugates by the MRP Gene–encoded Conjugate Export Pump", Jedlitschky, Leier, Buchholz, Barnouin, Kurz and Kejppler, Cancer Research, vol. 56(5), Mar. 1, 1996, pp. 988–994.

"ATP–dependent glutathone disulphide transport mediated by the MRP gene–encoded conjugate export pump", Leier, Jedlitschky, Buchholz, Center, Cole, Deeley and Keppler, Biochem. J., vol. 314(2), Mar. 1, 1996, pp. 433–437.

"Overexpression of the gene encoding the multidrug resistance–asociated protein results in increased ATP–dependent glutathone S–conjugate transport", Müller, Meijer, Zaman, Borst, Scheper, Mulder, E. De Vries and Jansen, Proc. Natnl. Acad. Sci., USA, vol. 91, Dec. 1994, pp. 13033–13037.

"Multidrug resistance proteins and other drug transport–related resistance to natural product agents", Broxterman, Giuseppe, Giaccone and Lankelma, Current Opinion in Oncology, vol. 7(6), Nov. 1995, pp. 532–540.

(List continued on next page.)

*Primary Examiner*—Jerome D. Goldberg
(74) *Attorney, Agent, or Firm*—Barnes & Thornburg

(57) ABSTRACT

This invention provides a method of identifying and reversing multidrug resistance in a multidrug resistance tumor comprising administering a multidrug resistance reversing amount of any of the compounds as defined herein.

2 Claims, 6 Drawing Sheets-

OTHER PUBLICATIONS

"The Leukotriene Ltd4 Receptor Antagonist MK571 Specifically Modulates MRP Associated Multidrug Resistance", Gekeler, Ise, Sanders, Ulrich and Beck, Biochemical and Biophysical Research Communications, vol. 208(1), Mar. 8, 1995, pp. 345–352.

"Expression of Multidrug resistance–associated protein (MRP) in anaplastic carcinoma of the thyroid", Sugawara, Arai, Yamashita, Yoshida, Masunaga and Itoyama, Cancer Letters, vol. 82, 1994, pp. 185–188.

"Expression of the Multidrug Resistance–Associated Protein (MRP) in Acute and Chronic Leukemias", Burger, Nooter, Zaman, Sonneveld, van Wingerden, Oostrum and Stoter, Leukemia, vol. 8(6), Jun. 1994, pp. 990–997.

"Increased Expression of the Multidrug Resistance–Associated Protein Gene in Relapsed Acute Leukemia", Schneider, Cowan, Bader, Toomey, Schwartz, Karp, Burke and Kaufmann, Blood 85: 1995, pp. 186–193.

"Membrane Transport Proteins Associated with Drug Resistance Expressed in Human Melanoma", Schadendorf, Makki, Stahr, van Dyck, Wanner, Scheffer, Flens, Scheper and Henz, American Journal of Pathology, vol. 147(6), Dec., 1995, pp. 1545–1552.

"Overexpression of a Transporter Gene in a Multidrug–Resistant Human Lung Cancer Cell Line", Cole, Bhardwaj, Gerlach, Mackie, Grant, Almquist, Stewart, Kurz, Duncan and Deeley, Science, vol. 258, Dec. 4, 1992, pp. 1650–1654.

ATP–dependent Transport of Glutathione S–Conjugates by the Multidrug Resistance–associated Protein[1], Jedlitschky, Leier, Buchholz, Cener and Keppler, Cancer Research, vol. 54, Sep. 15, 1994, pp. 4833–4836.

METHODS FOR IDENTIFYING AND TREATING RESISTANT TUMORS

CROSS-REFERENCE TO RELATED APPLICATIONS

This application is a continuation-in-part application of U.S. application Ser. No. 08/298,644 filed Aug. 31, 1994 (now U.S. Pat. No. 5,543,428 issued Aug. 6, 1996) and is a U.S. national phase counterpart of international application serial No. PCT/US95/11125 filed Aug. 31, 1995 which claims priority to U.S. application Ser. No. 08/298,644 filed Aug. 31, 1994, and German application serial no. P 44 32 563.0 filed Sep. 13, 1994.

BACKGROUND OF THE INVENTION

Along with surgery and radiotherapy, chemotherapy continues to be an effective therapy for many cancers. In fact, several types of cancer are now considered to be curable by chemotherapy and include Hodgkin's disease, large cell lymphoma, acute lymphocytic leukemia, testicular cancer and early stage breast cancer. Other cancers such as ovarian cancer, small cell lung and advanced breast cancer, while not yet curable, are exhibiting positive response to combination chemotherapy.

One of the most important unsolved problems in cancer treatment is drug resistance. Drug resistance includes both intrinsic resistance at the time of treatment using chemotherapy and acquired drug resistance. This problem is a reason for the added importance of combination chemotherapy, as the therapy both has to avoid the emergence of resistant cells and to kill pre-existing cells which are already drug resistant.

Anthracyclines represent an important class of oncolytic agents. Doxorubicin, an anthracycline, which is also known in the art as Adriamycin™, is a drug of choice in the clinical management of breast cancer. Therapy with anthracyclines such as doxorubicin is complicated by the appearance of the anthracycline resistant phenotype which limits or negates the oncolytic activity of doxorubicin.

Topoisomerase inhibitors represent a further class of oncolytic agents. Epipodophyllotoxins such as Etoposide® and Teniposide® are topoisomerase inhibitors which are useful in the therapy of neoplasms of the testis, small-cell lung and other lung, breast, Hodgkin's disease, non-Hodgkin's lymphomas, acute granulocytic leukemia and Karposi's sarcoma. The therapeutic utility of the epipodophyllotoxins is limited by the appearance of the epipodophyllotoxin resistant phenotype.

One form of multi-drug resistance (MDR) is mediated by a 170–180 kD energy-dependent efflux pump designated as P-glycoprotein, P-gp. P-gp has been shown to play a major role in the intrinsic and acquired resistance of a number of human tumors against hydrophobic, natural product drugs. Drugs that act as substrates for and are consequently detoxified by P-gp include the vinca alkaloids (vincristine and vinblastine), anthracyclines (Adriamycin), and epipodophyllotoxins (etoposide). While P-gp-associated MDR is a major determinant in tumor cell resistance to chemotherapeutic agents, it is clear that the phenomenon of MDR is multifactorial and involves a number of different mechanisms. One such alternative pathway for resistance to anthracyclines involves the emergence of a 190 kD protein that is not P-gp. See McGrath, T., Latoud, C., Arnold, S. T., Safa, A. R., Felsted, R. S., and Center, M. S. *Biochem. Pharmacol.*, 38: 3611, (1989). P190, also referred to as MRP, is found on the plasma membrane and also appears to be localized in the endoplasmic reticulum See Marquardt, D. and Center, M. S., *Cancer Res.*, 52: 3157, (1992).

MRP possesses a nucleotide binding domain that is homologous with the ATP binding site of P-gp. See Marquardt, D., McCrone, S., and Center M. S., *Cancer Res.*, 50: 1426, (1990). The mechanism(s) utilized by P190 to confer resistance to Adriamycin is not well understood but may involve the intracellular redistribution of Adriamycin away from the nucleus. See Marquardt, D. and Center, M. S., supra. Adriamycin is an inhibitor of topoisomerase II (Beck, W. T., *Bull. Cancer,* 77: 1131, (1990), which is an enzyme involved in DNA replication. Redistribution of Adriamycin away from the nucleus would therefore be an important component in cellular resistance to this drug. The studies published to date on P190 have utilized cell lines selected in vitro for resistance to Adrianycin (McGrath, T., Latoud, C., Arnold, S. T., Safa, A. R., Felsted, R. S., and Center, M. S., supra; Marquardt, D. and Center, M. S., supra; and Marquardt, D., McCrone, S., and Center M. S. *Cancer Res.*, supra. The association of MRP (P190) with drug resistance was made by sodium dodecyl sulfate polyacrylamide gel electrophoresis (SDS-PAGE) of radioactive extracts prepared from Adriamycin-resistant HL60/Adr human leukemia cells labeled with 8-azido-alpha[$^{32}$P]ATP. See McGrath, T., Latoud, C., Arnold, S. T., Safa, A. R., Felsted, R. S., and Center, M. S., supra. The drug-resistance phenotype conferred by P190 is not limited to the anthracyclines. Epipodophyllotoxin resistance is linked to P190 expression. The $IC_{50}$s of HL60/S cells treated with Adriamycin and Etoposide were 0.011 µg/ml and 0.39 µg/ml respectively. The $IC_{50}$S for HL60/Adr cells (a HL60-derived cell line which is resistant to doxorubicin) treated with Adriamycin and Etoposide were 2.2 µg/ml and >10 µg/ml respectively. HL60/S and HL60/Adr cell lines do not express P-glycoprotein. HL60/Adr expresses P190. Thus, resistance to the anthracyclines and epipodophyllotoxins results from P190 expression.

The present invention embraces the elucidation of the role which MRP plays in multiple drug resistance. MRP functions comprise an energy dependent transporter function to transport a range of oncolytics which include compounds which are generally conjugates of lipophilic compounds having anionic groups such as cysteinyl, carboxyl, cysteinylglycine, glutatione S, glucuronic acid or sulfate groups.

Biochemical characterization of the MRP protein allowed the development of MRP-based assays for compounds which reverse MDR by blocking the transport function of MRP, which in turn led to the identification of the compounds of the present invention.

SUMMARY OF THE INVENTION

The invention disclosed and claimed herein provides test kits and assay methodology for measuring MRP inhibition as well as compounds and associated formulations for use in reversing multiple drug resistance and thereby rendering otherwise refractory neoplasms susceptible to oncolytic therapies. The ability to determine the existence and extent of multiple drug resistance prior to attempts at therapy by evaluating a biopsy sample is a significant advance in the art and allows the elimination of costly and ineffective therapeutic attempts.

Compounds amenable to use in the invention are generally amphiphilic anions having a molecular weight of 300 to 950 and a molecular mass of 300 to 950 daltons respectively. Especially preferred multiple drug resistance compounds for use in accordance with the present invention include: MK571, BAY u9773 and compounds of Formula I:

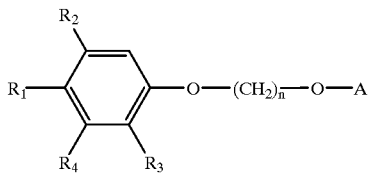

wherein

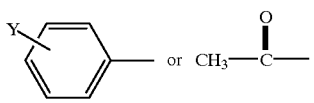

$R_1$ is
Y is hydrogen or halo;
$R_2$ is hydrogen, —OH, or —OCH$_3$;
$R_3$ is $C_1$–$C_6$ alkyl;
$R_4$ is hydrogen, —OH, or —OCH$_3$;
n is 3, 4, or 5;
and A is

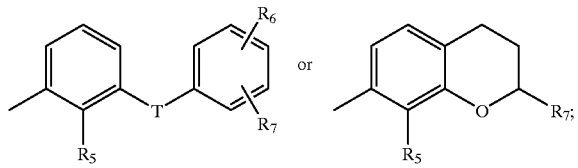

where
$R_5$ is hydrogen, $C_1$–$C_6$ alkyl, $C_2$–$C_5$ alkenyl, $C_2$–$C_5$ alkynyl, benzyl, or phenyl;
$R_6$ is hydrogen or halo;
$R_7$ is —COOH or 5-tetrazolyl;
T is a bond, —CH$_2$—, —O—, —C(=O)—, or —S(O)$_q$—; and
q is 0, 1, or 2;
provided when one of $R_2$ and $R_4$ is —OH or —OCH$_3$, the other of $R_2$ and $R_4$ must be hydrogen,
or a pharmaceutically acceptable base addition salt or solvate thereof.

DETAILED DESCRIPTION OF THE INVENTION

The present inventors have determined that a membrane protein which mediates the ATP-dependent transport of certain conjugates such as glucuronides and glutathione S-conjugates is associated with the cytostatic-agent resistance of certain tumors. The terms cytostatic agent, cytotoxic agent and oncolytic are used interchangeably to describe the present invention and these terms encompass the compounds used in cancer therapy regimens.

Elucidation of the substrate specificity of MRP allowed the selection and characterization of numerous compounds having multiple drug resistance reversal activity. Amphiphilic anions which are lipophilic compounds having a negative charge and a molecular weight of 300 to 950 (daltons), represent substrates for MRP and inhibit its ability to transport cytostatic agents out of the tumor cell again. Of particular interest are compounds which are usually conjugates of lipophilic compounds having anionic groups such as cysteinyl, carboxyl, cysteinylglycine, glutathione S, glucuronic acid or sulfate groups. The glutathione S-conjugate leukotriene C$_4$ as well as leukotrienes D$_4$ and E$_4$ were identified as substrates for the MRP protein, occurring naturally in the body. For this reason, substances structurally related to the leukotrienes C$_4$, D$_4$ and E$_4$ (LTC$_4$, LTD$_4$, LTE$_4$) are effective inhibitors for MRP. For example, cysteinyl leukotriene receptor antagonists are in consideration as substances structurally related to the leukotrienes. The receptor antagonists which react with C$_4$, D$_4$ and E$_4$ leukotriene receptors are also understood to include compounds structurally related to the receptor antagonists. The use of these inhibitors leads to an inhibition of MRP and thus to a drastic reduction of the cytostatic-agent resistance in tumors, e.g. in the case of bronchial carcinomas and leukemias. The compounds relevant to the present invention are grouped for description based on the extensive mechanistic data and assay kit development data which was generated using MK 571 and BAY u9773 versus the extensive synthetic chemistry effort directed to the phenoxy compounds of Formula I. Examples 1–18 describe the chemistry and cell-based assay system activity data relevant to the phenoxy compounds of Formula I.

Figure 1:
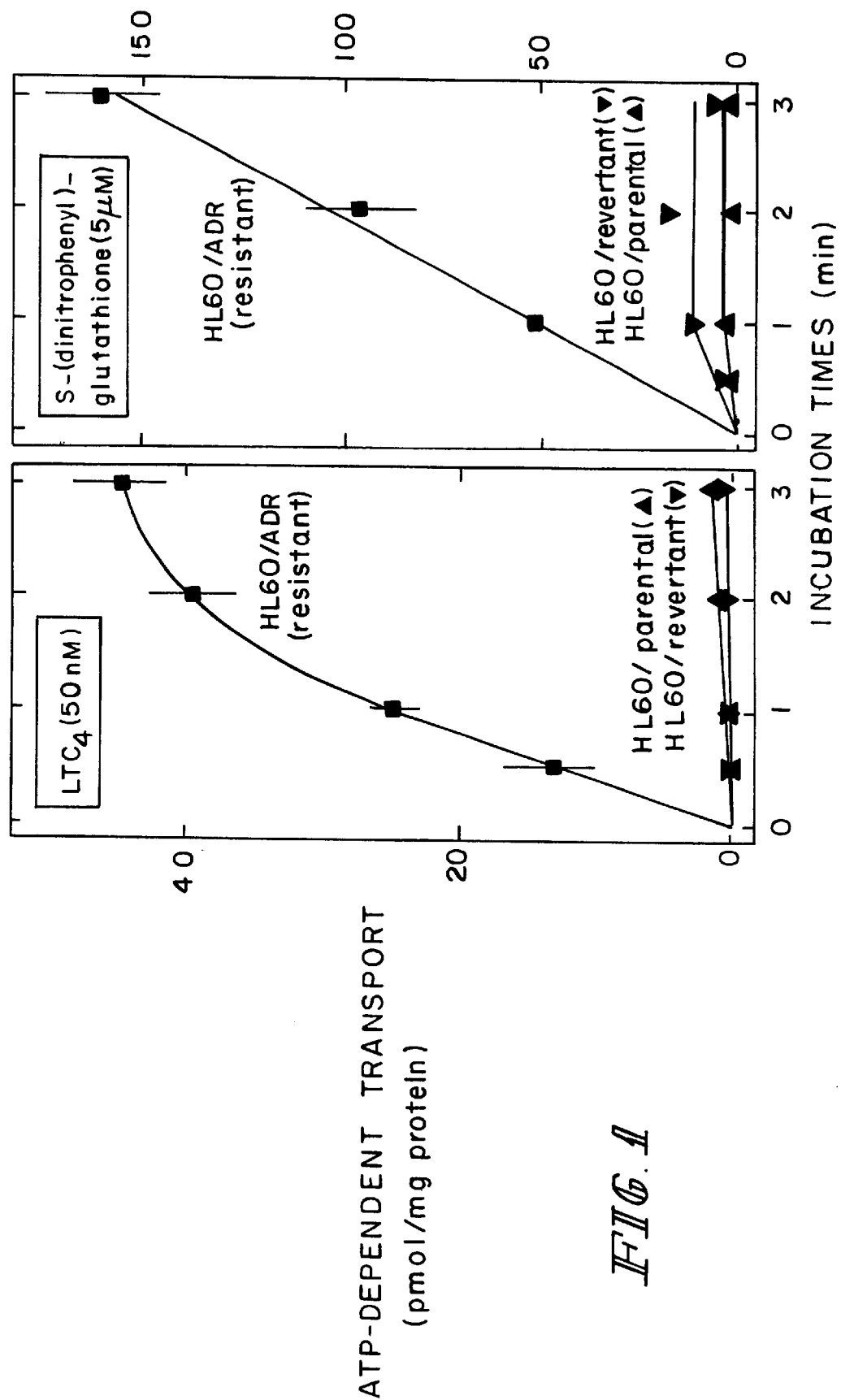
FIG. 1 shows the ATP-dependent transport of [$^3$H]LTC$_4$ (left-hand) and S-(2,4-dinitrophenyl)-[$^3$H]glutathione (right-hand side) by membrane vesicles of MRP-overexpressing HL60/ADR cells and control cells (cytostatic agent-sensitive parental cells as well as revertants)
Figure 2:
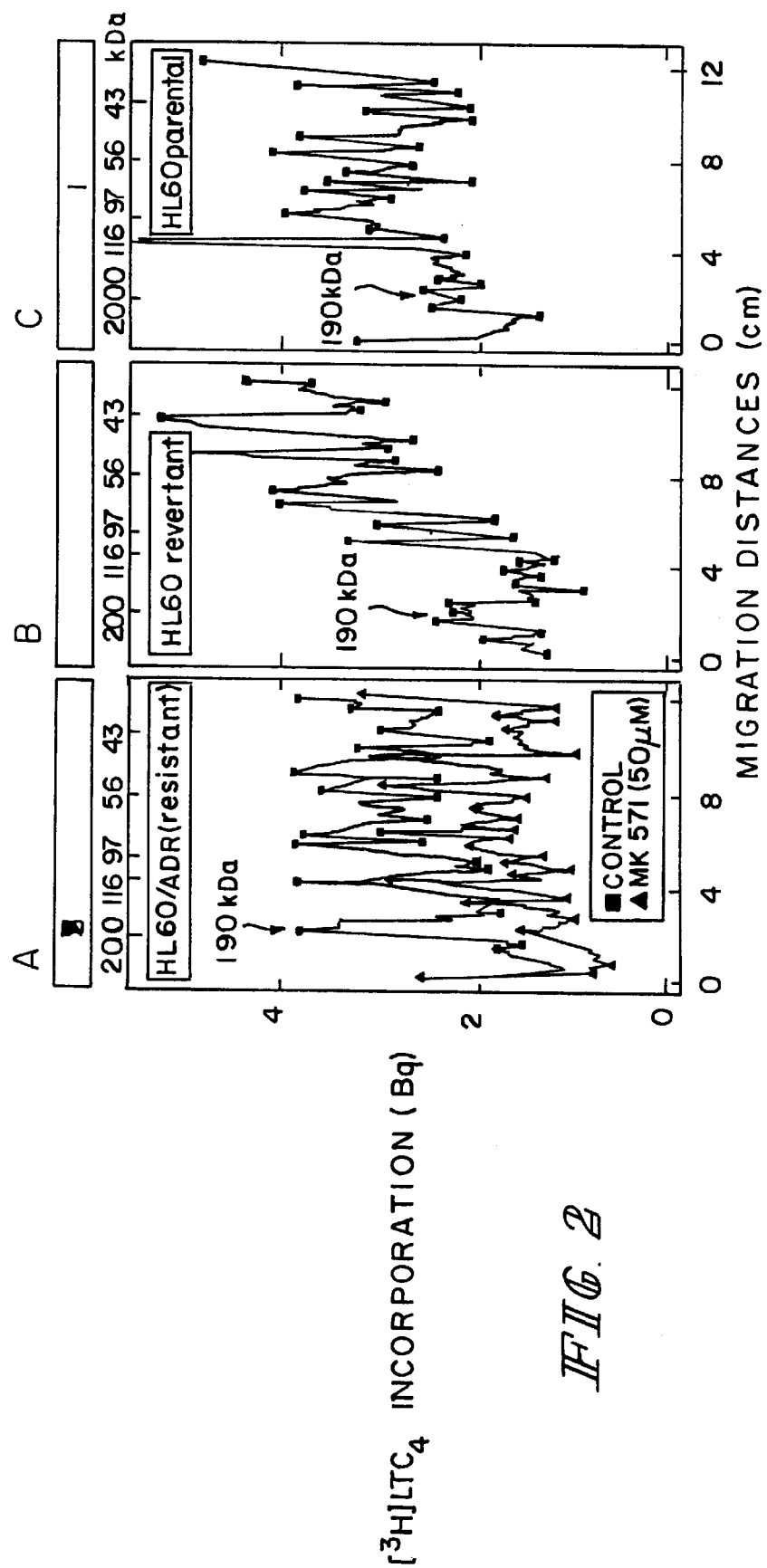
FIG. 2 shows [$^3$H]LTC4-binding proteins and immunoreactive MRP in membranes of HL60/ADR cells (A), revertant HL60 cells (B) and parental, cytostatic agent-sensitive HL60 cells (C). The top illustrates the evidence of MRP by immunoblot, the molecular weights of standard proteins following electrophoretic separation are shown therebelow, and the bottom illustrates the introduction of [$^3$H]LTC$_4$ after photoaffinity labeling and separation by SDS polyacrylamide electrophoresis. The suppression of the [$^3$H]LTC$_4$ labeling of HL60/ADR membranes by the transport inhibitor MK571 is shown in the left-hand illustration (A).
Figure 3:
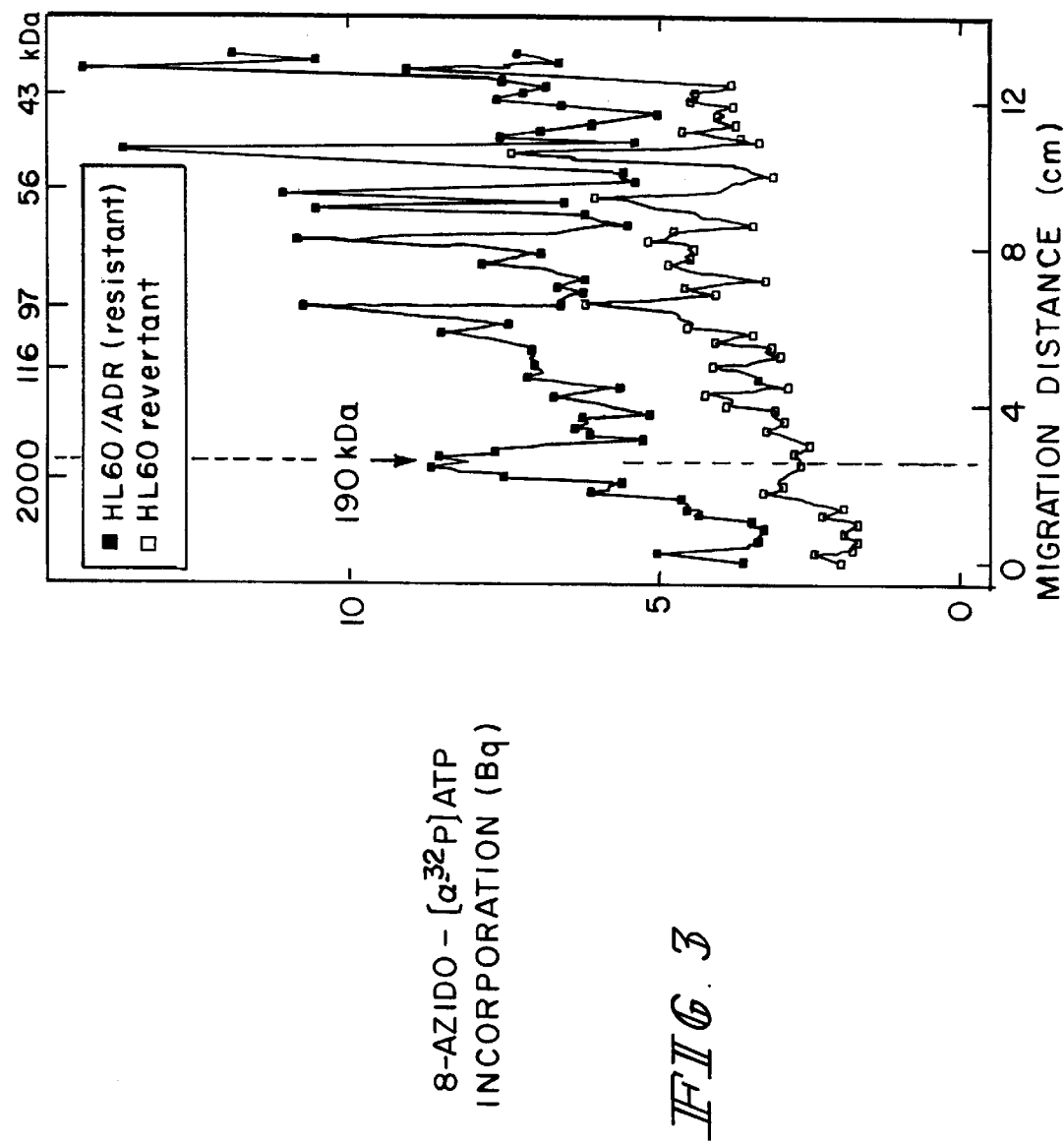
FIG. 3 shows 8-azido[α-$^{32}$P] ATP-binding proteins in membranes of HL60/ADR cells and revertant, cytostatic agent-sensitive cells.
Figure 4:
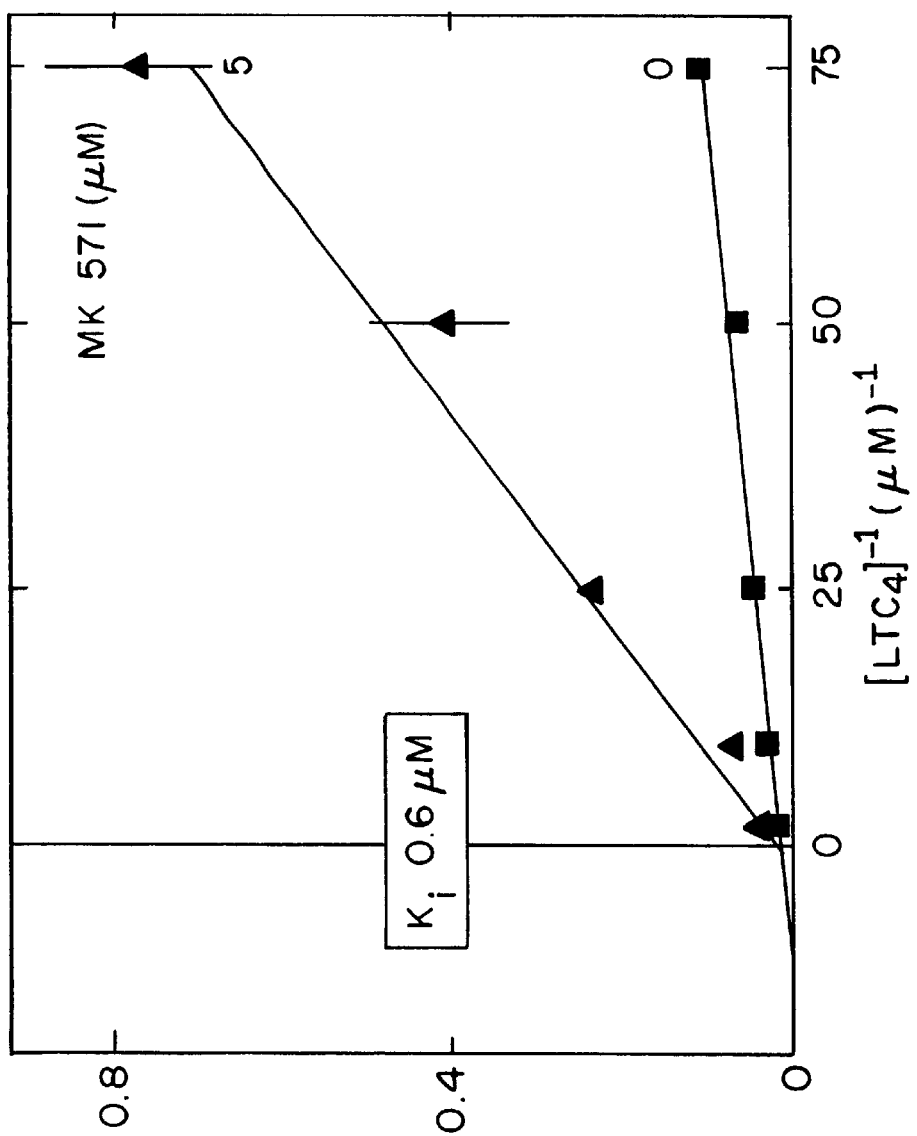
FIG. 4 shows the inhibition of the ATP-dependent transport of LTC$_4$ by the leukotriene receptor antagonist MK 571. The inhibition is shown in double-reciprocal (Lineweaver and Burk) plot. Membrane vesicles of MRP-overexpressing cells were incubated in the presence of ATP and LTC$_4$ at 37° C. for 2 minutes. Without the inhibitor (O), the transport activity is high, as also shown in FIG. 1 (left-hand side). MK 571 (5 micromolar) substantially inhibits transport. The inhibition is competitive. The inhibition constant ($K_i$) is 0.6 micromolar.
Figure 5:
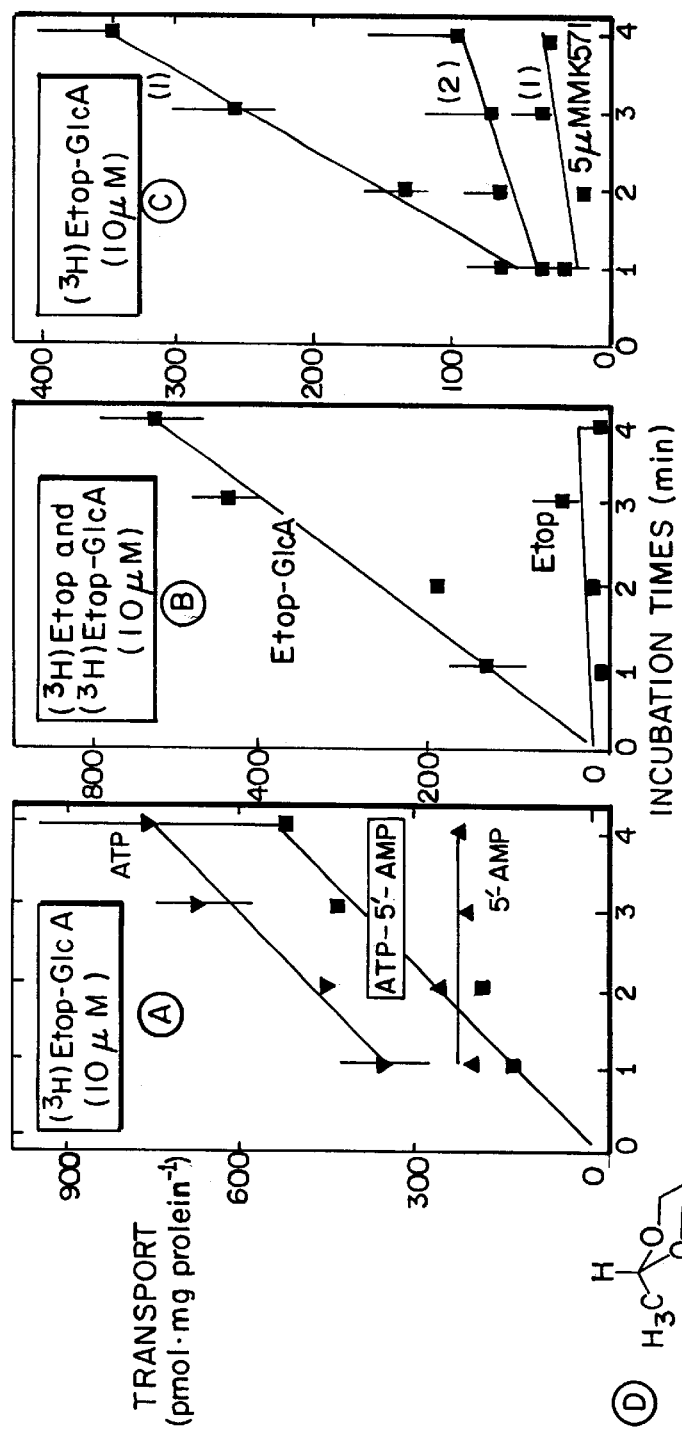
FIG. 5, Panel A illustrates the ATP-dependent transport of [$^3$H]etoposide glucuronide into membrane vesicles from MRP-overexpressing cells. Panel B provides a comparison of MRP-mediated ATP-dependent transport of [$^3$H] etoposide glucuronide and [$^3$H]etoposide into membrane vesicles from MRP-overexpressing cells. Panel C provides a comparison of MRP-mediated ATP-dependent transport of [$^3$H]etoposide glucuronide into membrane vesicles from MRP-overexpressing cells and controls cells and its inhibition by 5 µM MK 571. The structures of etoposide and etoposide glucuronide are provided in Panel D.
Figure 5:
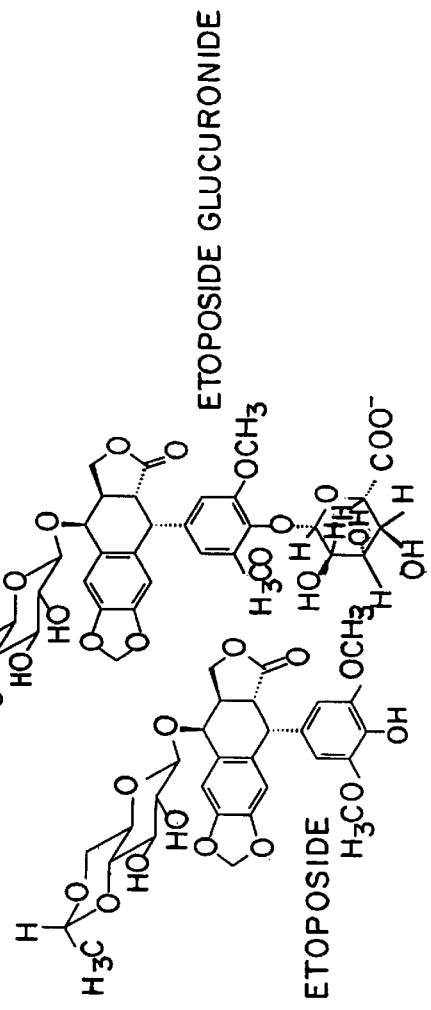
Figure 6:
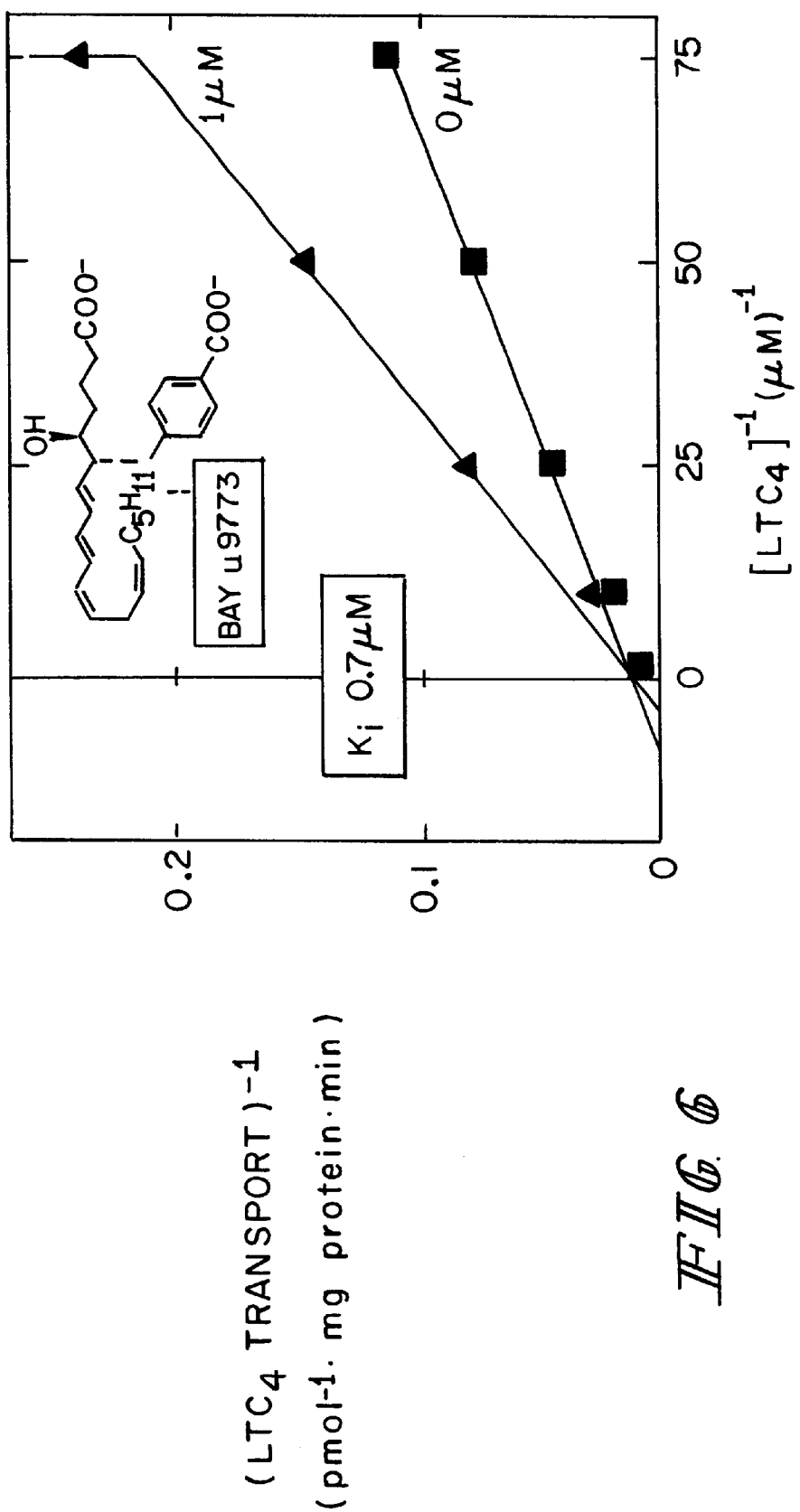
FIG. 6 illustrates the ATP-dependent transport of LTC4 into membrane vesicles from MRP-overexpressing cells and its competitive inhibition by the leukotriene receptor antagonist BAY u9773. The inhibition constant ($K_i$) is 0.7 micromolar.

A subset of leukotriene receptor antagonists of particular importance are those described in the scientific and patent literature in association with the bronchodilatation of asthma, e.g. MK 571 and BAY u9773. These compounds and their use in elucidating the mechanism of MRP and assay and kit development are further described below and in Examples 19–21 Results of transporter assays are summarized in FIGS. 1–6. The studies summarized in FIGS. 1–6 indicate that the preferred of the inhibitor at the site of action is 0.1 to 10 micromolar. The present inventors have further determined that a concentration of a MDR reversal agent of about 0.5 to to about 50 mg/kg body weight of the patient should be given to achieve the desired concentration at the site of action.

The methodology described in the Examples for evaluating various compounds for their ability to compete with radiolabeled leukotrienes for transport enables the preparation of various kits for measuring transport function or inhibition. Those of ordinary skill in the art will appreciate that various other "detector" groups such as fluorescent-labeled leukotrienes can be used in lieu of radioisotopes for providing a means to measure leukotriene transport or the inhibition thereof.

The following definitions refer to the various terms used throughout this disclosure to further describe the compounds of Formula I. The term "$C_1$–$C_6$ alkyl" refers to the straight and branched aliphatic radicals of 1 to 6 carbon atoms such as methyl, ethyl, propyl, isopropyl, n-butyl, sec-butyl, tert-butyl, n-pentyl, 2,2-dimethylpropyl, hexyl, and the like. Included within this definition are the terms "$C_1$–$C_3$ alkyl", "$C_1$–$C_4$ alkyl" and "$C_1$–$C_5$ alkyl". The term "$C_2$–$C_5$ alkenyl" refers to straight and branched aliphatic radicals of 2 to 5 carbon atoms containing one double bond, such as —CH=CH$_2$, —CH$_2$CH=CH$_2$, —CH$_2$CH$_2$CH=CH$_2$, —CH$_2$C(CH$_3$)=CH$_2$, —CH$_2$CH=C(CH$_3$)$_2$, and the like. The term "$C_2$–$C_5$ alkynyl" refers to straight and branched aliphatic residues of 2 to 5 carbon atoms containing one triple bond, such as —C≡CH, —CH$_2$—C≡CH, —CH$_2$CH$_2$C≡CH, —CH$_2$CH(CH$_3$)C≡CH, —CH$_2$C≡CCH$_3$, and the like. The term "halo" refers to fluoro, chloro, bromo, and iodo.

Preferred compounds of Formula I which are employed in this invention are those wherein $R_1$ is 4-halo (especially fluoro)phenyl or acetyl. In particular, compounds wherein

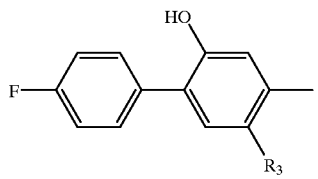

$R_1$–$R_4$-substituted phenyl is

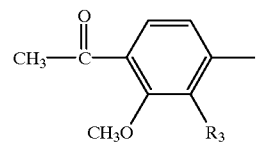

are preferred, especially when $R_3$ is propyl or ethyl. It is also preferred that $R_7$ is —COOH and $R_5$ is either propyl or benzyl. Compounds wherein A is

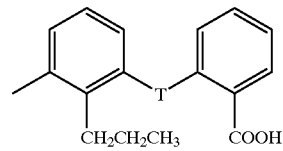

are especially preferred.

This invention includes the use of pharmaceutically acceptable base addition salts of the compounds of Formula I. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred. In addition, this invention includes any solvate forms of the compounds of Formula I or salts thereof, such as ethanol solvates, hydrates, and the like.

It is recognized that in compounds having a branched alkyl functionality, and in those compounds bearing double or triple bonds, various stereoisomeric products may exist. This invention is not limited to any particular stereoisomer but includes all possible individual isomers and mixtures thereof. The term "5-tetrazolyl" refers to both tautomers, i.e., (1H)-5-tetrazolyl and (2H)-5-tetrazolyl.

An important aspect of the current invention concerns the discovery that a select group of phenoxy compounds, those of Formula I, and the racemate and isomers of MK 571 and Bay u9771 are useful for treating resistant neoplasms. The synthesis of compounds of Formula 1 are taught in Examples 1–18. BAY u977 is commercially available from Cascade Biochem LTD, University Park, Whiteknights, Reading, Berkshire RG6 6BX, United Kingdom. MK571 and structurally related compounds of use in the present invention are taught in U.S. Pat. No. 5,350,761; U.S. Pat. No. 5,260,316; EP 526402-A1; U.S. Pat. No. 5,310,884; U.S. Pat. No. 5,155,130; EP 412,939-A; U.S. Pat. No. 5,120,758; U.S. Pat. No. 5,118,858; U.S. Pat. No. 5,428,171; U.S. Pat. No. 4,851,409; and EP 233763, the entire contents of which are hereby incorporated by reference. The methods of treatment provided by this invention are practiced by administering to a human or other mammal in need a multidrug resistance reversing amount of a compound of Formula I or a pharmaceutically acceptable salt or solvate thereof, that is effective to make the neoplasms less resistant to chemotherapy. In making the neoplasm less resistant, the compounds of the invention may be used on neoplasms having intrinsic and/or acquired resistance. Such neoplasms include those which have a pathway for resistance which includes the protein P190 (MRP). Resistance to drugs such as epipodophyllotoxins and anthracyclines are linked to P190. The treatment of the resistant and susceptible neoplasm will result in a reversal or inhibition of resistance, or in other words, will cause the neoplasm to be more sensitive to the appropriate chemotherapy such as treatment with vinblastine, vincristine, vindesine, navelbine, daunorubicin, doxorubicin, mitroxantrone, etoposide, teniposide, mitomycin C, actinomycin D, taxol, topotecan, mithramycin, colchicine, puromycin, podophyllotoxin, ethidium bromide, emetine, gramicidin D, and valinomycin.

The compounds of the invention may be used for many resistant neoplasms, including colon cancer, mesothelioma, melanoma, prostate cancer, ovarian cancer, non-small cell lung cancer, small-cell lung cancer, bladder cancer, endometrial cancer, leukemia, testicular cancer, breast cancer, and large cell lymphoma. More particular types of cancer are Hodgkin's disease, Karposi's sarcoma, and acute granulocytic leukemia.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like. Formulations containing more than one of the compounds of the present invention are also contemplated for use in the methods of the present invention.

The compounds of Formula I which can be beneficially used in the methods of the current invention can be made according to established procedures, such as those detailed in U.S. Pat. Nos. 5,324,743 and 4,889,871 and EPO Patent Applcation Publication 544,488, all of which are incorporated by reference herein.

The phenoxy compounds of Formula I employed in this invention are either disclosed in the two aforementioned references or can be prepared according to the same methods as disclosed therein. Other references for preparing other related compounds of this type, generally known as leukotriene antagonists, also provide the skilled organic chemist with methods for preparing such compounds.

The following preparations and examples further illustrate the preparation of the compounds employed in this invention. The examples are illustrative only and are not intended to limit the scope of the invention. Melting points were determined on a Thomas-Hoover apparatus and are uncorrected. NMR spectra were determined on a GE QE-300 spectrometer. All chemical shifts are reported in parts per million (∂) relative to tetramethylsilane. The following abbreviations are used to denote signal patterns: s=singlet, d=doublet, t=triplet, q=quartet, b=broad, m=multiplet. Infrared spectra were determined on a Nicolet DXIO FT-IR spectrometer. Mass spectral data were determined on a CEC-21-110 spectrometer using electron impact (EI) conditions, a MAT-731 spectrometer using free desorption (FD) conditions, or a VG ZAB-3F spectrometer using fast atom bombardment (FAB) conditions. Silica gel chromatography was performed using ethyl acetate/hexane gradients unless otherwise indicated. Reverse-phase chromatography was performed on MCI CHP20P gel using an acetonitrile/water or methanol/water gradient unless otherwise indicated. Tetrahydrofuran (THF) was distilled from sodium/benzophenone ketyl immediately prior to use. All reactions were conducted under argon atmosphere with stirring unless otherwise noted. Where structures were confirmed by infra-red, proton nuclear magnetic resonance, or mass spectral analysis, the compound is so designated by "IR", "NMR", or "MS", respectively.

EXAMPLE 1

8-Propyl-7-[3-[4-(4-fluorophenyl)-2-ethyl-5-hydroxyphenoxy]propoxy]-3,4-dihydro-2H-1-benzopyran-2-carboxylic acid

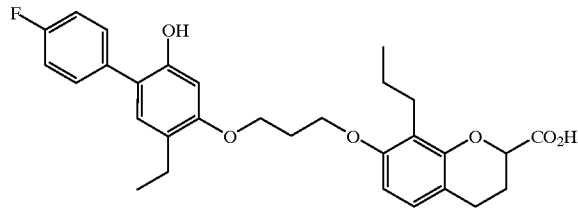

A. Preparation of ethyl 8-propyl-7-[3-[2-ethyl-4-(4-fluorophenyl)-5-benzyloxyphenoxy]propoxy]-3,4-dihydro-2H-1-benzopyran-2-carboxylate Tetrakis(triphenylphosphine)palladium(0) (0.659 g, 0.6 mmol) and aqueous sodium carbonate solution (20 mL of a 2M solution) were added to a 30 mL benzene solution of ethyl 7-[3-[(2-benzyloxy-1-bromo-5-ethyl-4-yl)oxy] propoxy]-3,4-dihydro-8-propyl-2H-1-benzopyran-2-carboxylate (2.163 g, 3.5 mmol) under an argon atmosphere. The reaction was refluxed for 17 hours, then cooled to room temperature and extracted with ethyl acetate. The organic extract was dried over magnesium sulfate, filtered and the solvent removed under vacuum. The crude product was purified by Waters Prep 500 silica gel chromatography eluting with a gradient of 5% to 20% ethyl acetate/hexane over 50 minutes. The desired title biphenyl was obtained as a clear oil (1.722 g, 78%).

NMR (CDCl$_3$) 7.51 (m, 2), 7.32 (m, 5), 7.09 (m, 3), 6.83 (d, 1, J=8.32 Hz), 6.62 (s, 1), 6.49 (d, 1, J=8.50 Hz), 5.02 (s, 2), 4.75 (dd, 1, J=4.10, 6.50 Hz), 4.22 (m, 6), 2.69 (m, 6), 2.25 (m, 4), 1.59 (m, 2), 1.30 (t, 3, J=7.10 Hz), 1.21 (t, 3, J=7.42 Hz), 0.96 (t, 3, J=7.33 Hz); IR (CHCl$_3$) 3019, 2968, 1745, 1611, 1495 cm$^{-1}$; Mass Spec. (FAB) (m/z) 627 (M$^+$+1), 626 (M$^+$), 536.

Analysis for C$_{39}$H$_{43}$O$_6$: Calc: C, 74.74; H, 6.91; F, 3.03; Found: C, 74.98, H, 7.05; F, 3.39.

B. Preparation of ethyl 8-propyl-7-[3-[4-(4-fluorophenyl)-2-ethyl-5-hydroxyphenoxy]propoxy]-3,4-dihydro-2H-1-benzopyran-2-carboxylate Hydrogen gas was bubbled for 10 minutes through a solution of ethyl 8-propyl-7-[3-[2-ethyl-4-(4-fluorophenyl)-5-benzyloxy-phenoxy]propoxy]-3,4-dihydro-2H-1-benzopyran-2-carboxylate (1.610 g, 2.57 mmol) in 30 mL of ethyl acetate containing 1.0 g of 10% Pd/C catalyst. The reaction was stirred at room temperature under an atmosphere of hydrogen for 2 hours. The reaction mixture was filtered through a Celite® pad in a sintered glass funnel and the catalyst was washed with ethyl acetate. The solvent was removed from the filtrate providing 1.242 g of a clear oil. The oil was purified by flash chromatography on Merck silica gel eluting with 20% ethyl acetate/hexane. The desired title phenol was obtained in 74% yield (1.020 g) as a white solid.

TLC: Rf=0.35 (30% ethyl acetate/hexane)

NMR (CDCl$_3$) 7.43 (m, 2), 7.16 (dd, 2, J=5.97, 5.97 Hz), 6.98 (s, 1), 6.82 (d, 1, J=8.44 Hz), 6.53 (s, 1), 6.46 (d, 1,

J=9.43 Hz), 5.07 (s, 1), 4.76 (m, 1), 4.21 (m, 6), 2.67 (m, 6), 2.26 (m, 4), 1.58 (m, 2), 1.29 (t, 3, J=6.96 Hz), 1.91 (t, 3, J=7.35 Hz), 0.96 (t, 3, J=7.27 Hz);

IR (KBr) 3434, 2962, 2869, 1738, 1614, 1588, 1502 cm$^{-1}$;

Mass Spec (FAB) (m/z) 537 (M$^+$+1), 536 (M$^+$).

Analysis for $C_{32}H_{37}O_6$: Calc: C, 71.62; H, 6.95; Found: C, 71.63; H, 7.06.

C. Preparation of 8-propyl-7-[3-[4-(4-fluorophenyl)-2-ethyl-5-hydroxyphenoxy]propoxy]-3,4-dihydro-2H-1-benzopyran-2-carboxylic acid A dioxane (12 mL) solution of ethyl 8-propyl-7-[3-[4-(4-fluorophenyl)-2-ethyl-5-hydroxyphenoxy]propoxy]-3,4-dihydro-2H-1-benzopyran-2-carboxylate (0.968 g, 1.8 mmol) was treated with sodium hydroxide (2.71 mL of a 2N solution) and stirred at room temperature. After 2.5 hours at room temperature, the dioxane was removed from the reaction mixture and the remaining material was diluted with water and acidified to pH 1 with 5N hydrochloric acid. The resulting white milky suspension was then stirred with ethyl acetate and subsequently extracted with ethyl acetate. The organic extract was dried over magnesium sulfate, filtered and the solvent removed to give a white solid (1.098 g). The solid was recrystallized from ethyl acetate/hexane to give the title acid as white needle-like crystals (0.568 g, 62%).

TLC: Rf=0.31 (10% methanol/methylene chloride)

NMR (CDCl$_3$) ∂ 7.42 (m, 2), 7.15 (dd, 2, J=8.68), 6.98 (s, 1), 6.85 (d, 1, J=8.30 Hz), 6.53 (s, 1), 6.52 (d, 1, J=6.98 Hz), 4.77 (dd, 1, J=3.63, 7.43 Hz), 4.18 (m, 4), 2.70 (m, 6), 2.27 (m, 4), 1.56 (m, 2), 1.19 (t, 3, J=7.42 Hz), 0.95 (t, 3, J=7.30 Hz); IR (KBr) 3421, 2959, 2871, 1706, 1615, 1500 cm$^{-1}$; Mass Spec (FAB) (m/z) 509 (M$^+$+1), 508 (M$^+$).

Analysis for $C_{30}H_{33}O_6$: Calc: C, 70.78; H, 6.54; Found: C, 70.05; H, 6.82.

EXAMPLE 2

2-[2-Propyl-3-[3-(2-ethyl-5-hydroxy-4-phenylphenoxy)-propoxy]phenoxy]benzoic acid sodium salt hemihydrate A. Preparation of 2-(3-hydroxy-2-propylphenoxy)-benzoic acid methyl ester A mixture of 1,3-dihydroxy-2-propylbenzene (75.0 g, 0.490 mol), methyl 2-iodobenzoate (129 g, 0.490 mol), copper bronze (47.0 g, 0.740 mol) and potassium carbonate (81.7 g, 0.592 mol) in dry pyridine (1 L) was thoroughly de-gassed with nitrogen, then refluxed for 6 hours. The mixture was cooled to room temperature, filtered, and concentrated in vacuo to reveal a dark sludge. This material was dissolved in ethyl acetate and passed down a short (~500 cm$^3$) Florisil® column. The resulting solution was washed twice with a saturated copper sulfate solution and concentrated in vacuo. The residue was dissolved in methylene chloride, washed once with a 0.5 N sodium hydroxide solution, and washed once with a dilute sodium hydroxide solution. The organic layer was dried over sodium sulfate, filtered, and concentrated in vacuo to provide a clear brown oil. Silica gel chromatography (ethyl acetate/hexane) provided 45.4 g (32%) of the desired title intermediate as a white solid: mp 80° C.; NMR (CDCl$_3$) 7.92 (dd, J=7.8, 1.6 Hz, 1H), 7.42 (t, J=8.4 Hz, 1H), 7.13 (t, J=7.2 Hz, 1H), 6.97 (t, J=8.1 Hz, 1H), 6.86 (d, J=8.1 Hz, 1H), 6.62 (d, J=8.0 Hz, 1H), 6.51 (d, J=8.0 Hz, 1H), 5.65 (bs, 1H, —OH), 3.88 (s, 3H), 2.66 (t, J=7.6 Hz, 2H), 1.62 (hextet, J=7.6 Hz, 2H), 0.96 (t, J=7.4 Hz, 3H); MS-FD m/e 286 (p); IR (CHCl$_3$, cm$^{-1}$) 3350 (b), 2950, 1718, 1602, 1480, 1306, 1255, 1086, 981.

Analysis for $C_{17}H_{18}O_4$: Calc: C, 71.31; H, 6.34; Found: C, 71.53; H, 6.37.

B. Preparation of 2-[2-propyl-3-[3-(2-ethyl-5-hydroxy-4-phenylphenoxy)propoxy]phenoxy]benzoic acid sodium salt hemihydrate 2-(3-Hydroxy-2-propylphenoxy)benzoic acid methyl ester (450 mg, 1.57 mmol) was alkylated with 2-benzyloxy-1-phenyl-5-ethyl-4-(3-chloro-1-propyloxy)benzene, de-benzylated, and hydrolyzed. Salt formation and purification provided 200 mg (21%) of the desired title product as a fluffy white solid: NMR (DMSO-d$_6$) 7.48 (d, J=7.5 Hz, 2H), 7.42 (d, J=7.2 Hz, 1H), 7.31 (t, J=7.4 Hz, 2H), 7.18 (t, J=7.5 Hz, 1H), 7.16 (t, J=7.1 Hz, 1H), 6.98 (m, 3H), 6.64 (t, J=7.2 Hz, 2H), 6.60 (s, 1H), 6.24 (d, J=7.9 Hz, 1H), 4.15 (m,

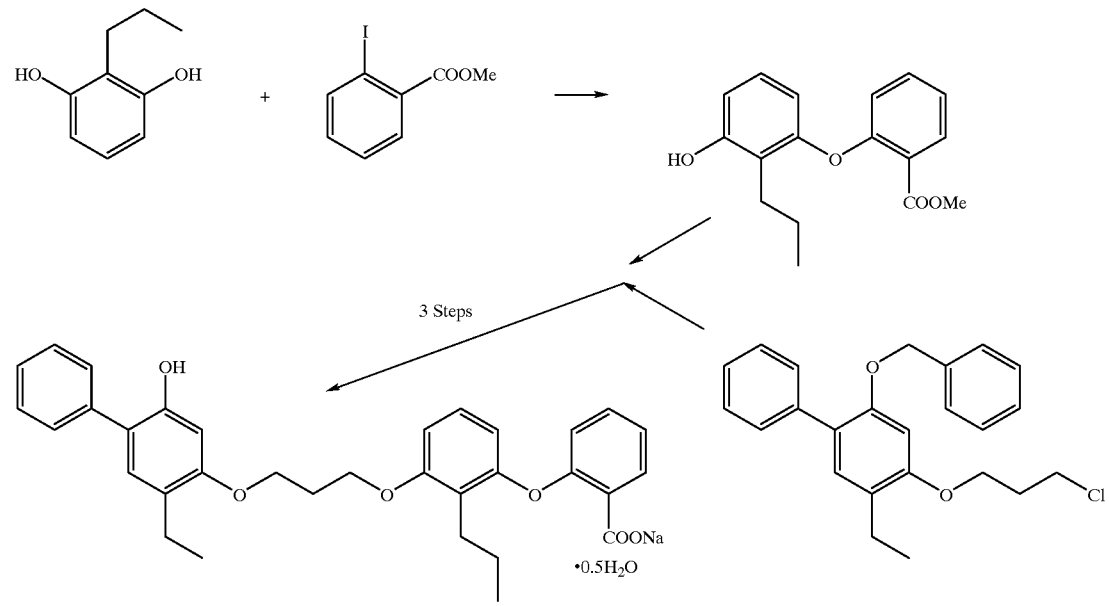

2H), 4.02 (m, 2H), 2.61 (m, 2H), 2.49 (m, 2H), 2.16 (t, J=5.5 Hz, 2H), 1.46 (hextet, J=6.6 Hz, 2H), 1.07 (t, J=7.4 Hz, 3H), 0.82 (t, J=7.4 Hz, 3H); MS-FAB m/e 549 (100, p+1), 526 (32), 295 (28), 252 (34), 227 (20), 213 (21); IR (CHCl$_3$, cm$^{-1}$) 3450 (b), 2974, 1602, 1586, 1461, 1393, 1240, 1113, 1048.

Analysis for C$_{33}$H$_{32}$O$_6$Na.0.5 H$_2$O: Calc: C, 71.22; H, 5.94; Found: C, 71.42; H, 6.16.

EXAMPLE 3

5-Ethyl-4-[3-[2-propyl-3-[2-(2H-tetrazol-5-yl)phenoxy]phenoxy]propoxy][1,1'-biphenyl]-2-ol disodium salt sesquihydrate

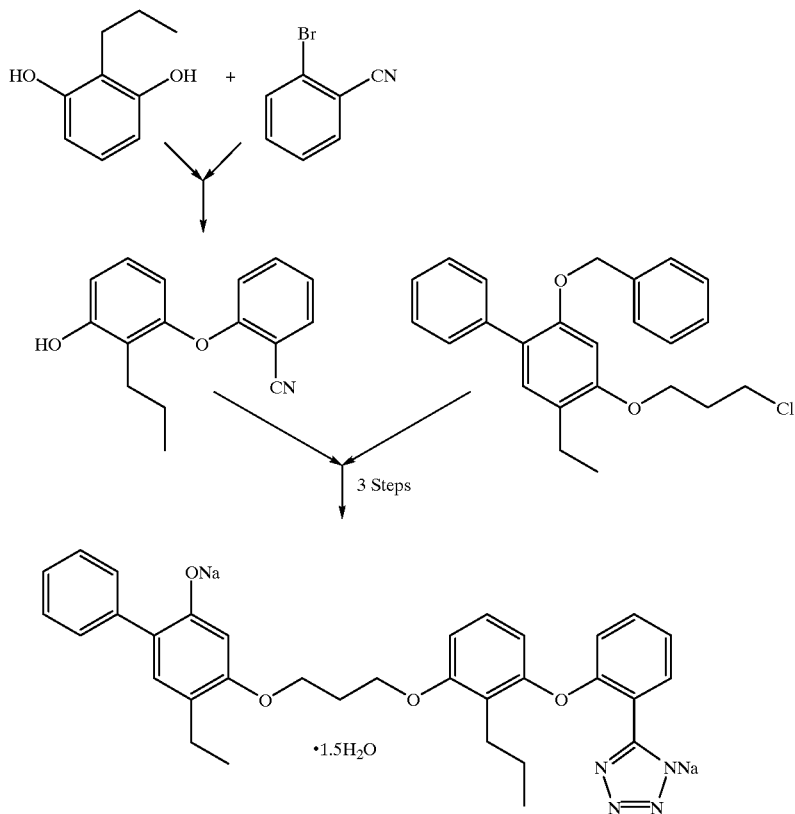

A. Preparation of 3-(2-cyanophenoxy)-2-propylphenol

A mixture of 3-hydroxy-2-propylphenol (7.50 g, 49.3 mmol), 2-bromobenzonitrile (8.97 g, 49.3 mmol), copper bronze (3.76 g, 59.2 mmol), and potassium carbonate (6.80 g, 49.3 mmol) in pyridine (250 mL) was refluxed for 72 hours. The mixture was cooled to room temperature, filtered, and concentrated in vacuo. The residue was dissolved in ethyl acetate and washed once with water and three times with a saturated copper sulfate solution. The organic layer was dried over sodium sulfate, filtered, and concentrated in vacuo to provide a dark oil. Silica gel chromatography provided a white solid. Sublimation of this material (bulb-to-bulb distillation apparatus, 200° C.) to remove excess 3-hydroxy-2-propylphenol provided 1.79 g (14%) of the desired title intermediate as an off-white crystalline material: mp 103–107° C.; NMR (CDCl$_3$) 7.68 (d, J =8 Hz, 1H), 7.47 (t, J=7 Hz, 1H), 7.12 (t, J=8 Hz, 1H), 7.10 (t, J=8 Hz, 1H), 6.80 (d, J=9 Hz, 1H), 6.71 (d, J=9 Hz, 1H), 6.58 (d, J=9 Hz, 1H), 4.95 (s, 1H, —OH), 2.62 (t, J=7 Hz, 2H), 1.60 (hextet, J=6 Hz, 2H), 0.96 (t, J=7 Hz, 3H); MS-FD m/e 253 (p); IR (CHCl$_3$, cm$^{-1}$) 3300 (b), 2967, 2234, 1600, 1485, 1483, 1450, 1247, 1097, 980.

Analysis for C$_{16}$H$_{15}$NO$_2$: Calc: C, 75.87; H, 5.97; N, 5.53; Found: C, 75.09; H, 5.88; N, 5.58.

B. Preparation of 5-ethyl-4-[3-[2-propyl-3-[2-(2H-tetrazol-5-yl)phenoxy]propoxy][1,1'-biphenyl]-2-ol disodium salt sesquihydrate 3-(2-Cyanophenoxy)-2-propylphenol (1.66 g, 6.56 mmol) was alkylated with 2-benzyloxy-1-phenyl-5-ethyl-4-(3-chloro-1-propyloxy)benzene. The crude product was dissolved in hexane/ethyl acetate and passed through a short silica gel column. The solution was concentrated in vacuo and the residue dissolved in 2-methoxyethanol (50 mL). To this solution was added lithium azide (1.38 g, 24.2 mmol) and triethylammonium bromide (1.30 g, 7.14 mmol). The resulting mixture was refluxed for 48 hours, cooled to room temperature, and passed down a short silica gel column. The column was washed with excess ethyl acetate and the combined washings were concentrated in vacuo. The resulting material was de-benzylated and the crude tetrazole was converted to the sodium salt and purified to provide 320 mg (8%) of the desired title product as a fluffy white solid: NMR (DMSO-d$_6$) 7.81 (dd, J =7.7, 1.5 Hz, 1H), 7.49 (d, J=7.5 Hz, 2H), 7.33 (t, J=7.5 Hz, 2H), 7.21 (m, 2H), 7.11 (t, J=7.3 Hz, 1H), 6.99 (m, 2H), 6.76 (d, J=8.1 Hz, 1H), 6.68 (d, J=8.2 Hz, 1H), 6.56 (s, 1H), 6.22 (d, J=8.2 Hz, 1H), 4.16 (t, J=5.8 Hz, 2H), 4.10 (t, J=5.9 Hz, 2H), 2.61 (t, J=6.5 H, 2H), 2.48 (m, 2H), 2.22 (m, 2H), 1.45 (hextet, J=7.4 Hz, 2H), 1.08 (t, J=7.4 Hz, 3H), 0.79 (t, J=7.3 Hz, 3H); MS-FAB m/e 595 (35, p+1), 574 (39), 573 (100), 551(99); IR (KBr, cm$^{-1}$) 3418 (b), 2962, 1577, 1458, 1243, 1229, 1147, 1117.

Analysis for C$_{33}$H$_{32}$N$_4$O$_4$Na$_2$.1.5 H$_2$O: Calc: C, 63.76; H, 5.68; N, 9.01; Found: C, 63.63; H, 5.59; N, 8.80.

EXAMPLE 4

2-Fluoro-6-[2-propyl-3-[3-(2-ethyl-5-hydroxy-4-phenylphenoxy)propoxy]phenoxy]benzoic acid disodium salt

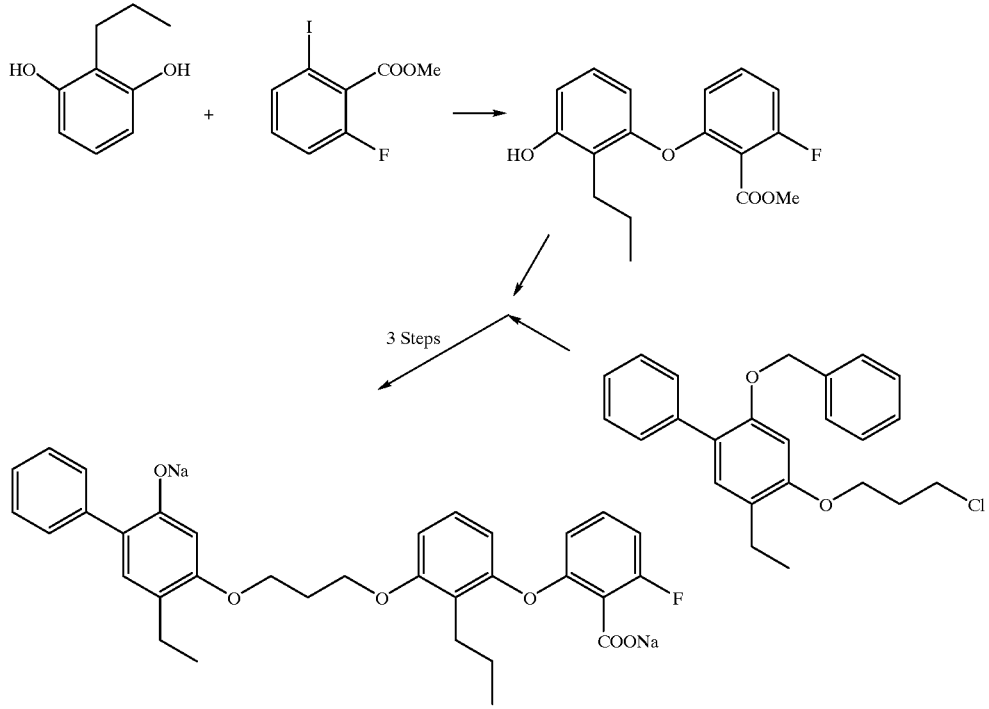

A. Preparation of 2-fluoro-6-(3-hydroxy-2-propylphenoxy)benzoic acid methyl ester 2-Fluoro-6-iodobenzoic acid methyl ester (13.1 g, 46.8 mmol) was submitted to the Ullmann conditions. This procedure provided 3.10 g (22%) of the desired title intermediate as an oil: NMR (CDCl$_3$) 7.26 (m, 1H), 7.03 (t, J=8.1 Hz, 1H), 6.83 (t, J=8.6 Hz, 1H), 6.65 (d, J=8.0 Hz, 1H), 6.56 (d, J=7.8 Hz, 1H), 6.53 (d, J=7.6 Hz, 1H), 5.30 (bs, 1H, —OH), 3.93 (s, 3H), 2.59 (t, J=7.3 Hz, 2H), 1.56 (hextet, J=7.6 Hz, 2H), 0.94 (t, J=7.4 Hz, 3H).

B. Preparation of 2-fluoro-6-(2-propyl-3-[3-(2-ethyl-5-hydroxy-4-phenylphenoxy)propoxy]phenoxy]benzoic acid disodium salt 2-Fluoro-6-(3-hydroxy-2-propylphenoxy)benzoic acid methyl ester (0.660 g, 2.17 mmol) was alkylated with 2-benzyloxy-1-phenyl-5-ethyl-4-(3-chloro-1-propyloxy) benzene to provide crude product as an oil. The oil was de-benzylated, hydrolysed, salified, and purified to provide 468 mg (37%) of the desired title product as a fluffy white solid: NMR (DMSO-d$_6$) 7.49 (d, J=8.8 Hz, 2H), 7.32 (t, J =7.5 Hz, 2H), 7.18 (t, J=7.4 Hz, 1H), 6.85–7.10 (m, 3H), 6.74 (t, J=8.1 Hz, 2H), 6.62 (s, 1H), 6.42 (d, J=8.1 Hz, 1H), 6.33 (d, J=8.2 Hz, 1H), 4.13 (t, J=6.0 Hz, 2H), 4.04 (t, J=5.8 Hz, 2H), 2.40–2.63 (m, 4H), 2.15 (m, 2H), 1.41 (hextet, J=7.3 Hz, 2H), 1.07 (t, J=7.4 Hz, 3H), 0.79 (t, J=7.2 Hz, 3H); MS-FAB m/e 589 (16, p), 568 (36), 567 (100), 546 (30), 527 (15); IR (CHCl$_3$, cm$^{-1}$) 2975, 1601, 1456, 1395, 1115, 1047.

Analysis for C$_{33}$H$_{31}$O$_6$FNa$_2$: Calc: C, 67.34; H, 5.31; F, 3.23; Found: C, 67.43; H, 5.59; F, 2.99.

EXAMPLE 5

2-[2-Propyl-3-[3-[2-ethyl-4-(4-fluorophenyl)-5-hydroxyphenoxy]propoxy]phenoxy]benzoic acid sodium salt

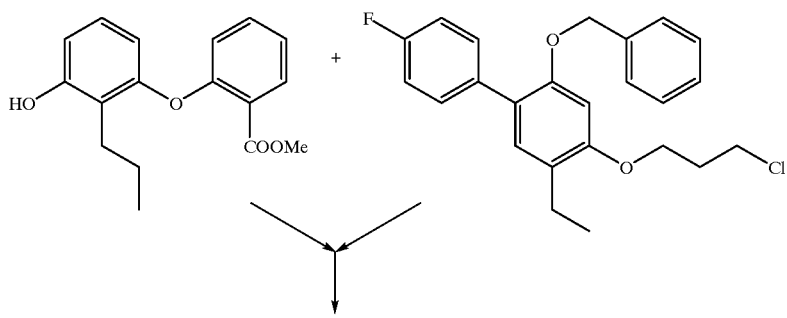

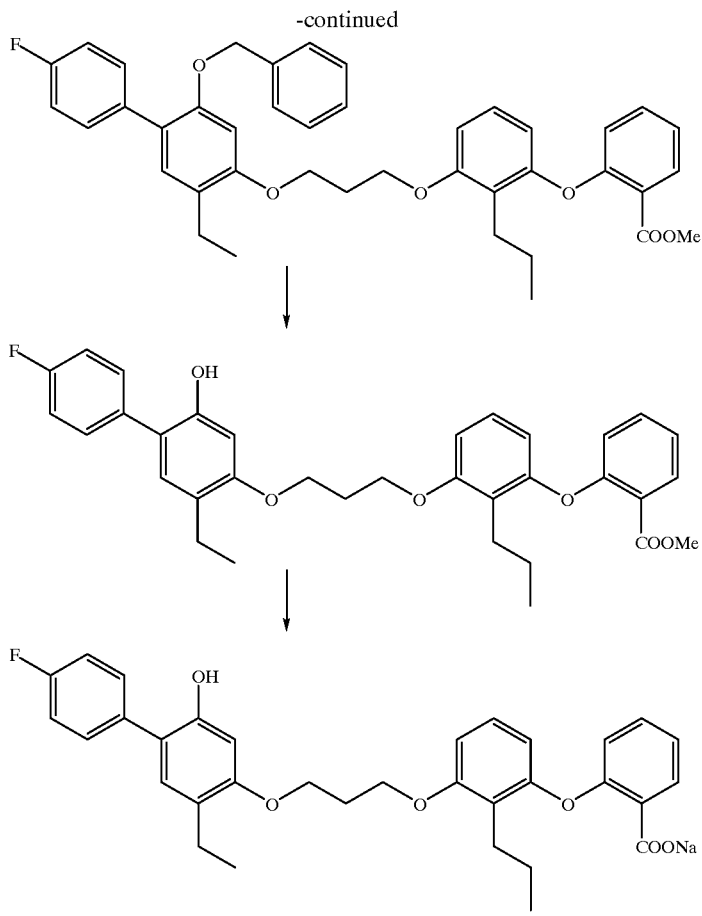

A. Preparation of 2-[2-propyl-3-[3-[2-ethyl-4-(4-fluorophenyl)-5-(phenylmethoxy)phenoxy]propoxy]phenoxy]benzoic acid methyl ester A mixture of 2-benzyloxy-1-(4-fluorophenyl)-5-ethyl-4-(3-chloro-1-propyloxy)benzene (20.0 g, 50.2 mmol) and sodium iodide (75.3 g, 502 mmol) in 2-butanone (200 mL) was refluxed for 6 hours. The mixture was diluted with ether and washed once with water. The organic layer was dried over sodium sulfate, filtered, and concentrated in vacuo to provide a colorless oil. This material was dissolved in dimethylformamide 1100 mL) and treated with 2-(3-hydroxy-2-propylphenoxy)benzoic acid methyl ester (14.4 g, 50.2 mmol) and potassium carbonate (20.8 g, 151 mmol) at room temperature for 24 hours. This mixture was diluted with water and twice extracted with ether. The aqueous layer was separated and back-extracted once with ethyl acetate. The combined organic layers were dried over sodium sulfate, filtered, and concentrated in vacuo to provide a yellow oil. Silica gel chromatography provided 25.4 g (78%) of the desired title intermediate as a pale golden oil: NMR (CDCl$_3$) 7.91 (∂, J=7.8 Hz, 1H), 7.54 (d, J=8.6 Hz, 1H), 7.52 (d, J=8.5 Hz, 1H), 7.25–7.43 (m, 6H), 7.03–7.38 (m, 5H), 6.84 (d, J=8.3 Hz, 1H), 6.71 (d, J=8.1 Hz, 1H), 6.63 (s, 1H), 6.47 (d, J=8.1 Hz, 1H), 5.03 (s, 2H), 4.24 (t, J=5.7 Hz, 2H), 4.21 (t, J=5.8 Hz, 2H), 3.86 (s, 3H), 2.69 (t, J=7.8 Hz, 2H), 2.64 (t, J=7.7 Hz, 2H), 2.34 (quintet, J=6.0 Hz, 2H), 1.60 (hextet, J=5.0 Hz, 2H), 1.22 (t, J=7.5 Hz, 3H), 0.94 (t, J=7.5 Hz, 3H); MS-FD m/e 648 (p); IR (CHCl$_3$, cm$^{-1}$) 2960, 1740, 1604, 1497, 1461, 1112.

Analysis for C$_{41}$H$_{41}$O$_6$F: Calc: C, 75.91; H, 6.37; Found: C, 76.15; H, 6.45.

B. Preparation of 2-[2-propyl-3-[3-[2-ethyl-4-(4-fluorophenyl)-5-hydroxyphenoxy]propoxy]phenoxy] benzoic acid methyl ester 2-[2-Propyl-3-[3-[2-ethyl-4-(4-fluorophenyl)-5-(phenylmethoxy)phenoxy]propoxy]phenoxy]benzoic acid methyl ester (33.0 g, 50.9 mmol) was de-benzylated to provide 27.3 g (96%) of the title intermediate as an amber oil: NMR (CDCl$_3$) 7.90 (dd, J=7.8, 1.7 Hz, 1H), 7.42 (m, 3H), 7.05–7.23 (m, 4H), 6.99 (s, 1H), 6.84 (d, J=8.1 Hz, 1H), 6.70 (d, J=8.1 Hz, 1H), 6.55 (s, 1H), 6.46 (d, J=8.1 Hz, 1H), 5.05 (s, 1H, —OH), 4.23 (m, 4H), 3.86 (s, 3H), 2.68 (t, J=7.4 Hz, 2H), 2.62 (q, J=7.5 Hz, 2H), 2.36 (quintet, J=6.0 Hz, 2H), 1.60 (hextet, J=7.7 Hz, 2H), 1.20 (t, J=7.6 Hz, 3H), 0.94 (t, J=7.4 Hz, 3H); MS-FD m/e 558 (p); IR (CHCl$_3$, cm$^{-1}$) 2965, 1727, 1603, 1496, 1458, 1306, 1112.

Analysis for C$_{34}$H$_{35}$O$_6$F: Calc: C, 73.10; H, 6.31; Found: C, 73.17; H, 6.42.

C. Preparation of 2-[2-propyl-3-[3-[2-ethyl-4-(4-fluorophenyl)-5-hydroxyphenoxy]propoxy]phenoxy] benzoic acid sodium salt 2-[2-Propyl-3-[3-[2-ethyl-4-(4-fluorophenyl)-5-hydroxyphenoxy]propoxy]phenoxy]benzoic acid methyl ester (21.5 g, 38.5 mmol) was hydrolyzed. The resulting acid was converted to the sodium salt and purified to provide 16.7 g (77%) of the desired title product as a white amorphous solid: NMR (DMSO-d$_6$) 10.50 (bs, 1H, —OH), 7.51 (m, 3H), 7.20 (t, J=7.4 Hz, 1H), 7.13 (m, 2H), 7.00 (m, 2H), 6.95 (s, 1H), 6.67 (dd, J=8.2, 3.3 Hz, 2H), 6.62 (s, 1H), 6.26 (d, J=8.2 Hz, 1H), 4.14 (t, J=5.8 Hz, 2H), 4.02 (t, J=5.7 Hz, 2H), 2.60 (t, J=6.8 Hz, 2H), 2.47 (q, J=7.3 Hz, 2H), 2.16 (t, J=5.9

Hz, 2H), 1.45 (hextet, J=7.5 Hz, 2H), 1.07 (t, J=7.5 Hz, 3H), 0.81 (t, J=7.4 Hz, 3H); MS-FAB m/e 568 (38, p+1), 567 (100, p), 544 (86), 527 (77), 295 (65), 253 (45); IR (KBr, cm$^{-1}$) 3407 (b), 2962, 1603, 1502, 1446, 1395, 1239, 1112.

Analysis for $C_{33}H_{32}O_6FNa$: Calc: C, 69.95; H, 5.69; F, 3.35; Found: C, 69.97; H, 5.99; F, 3.52.

EXAMPLE 6

2-Fluoro-6-[2-propyl-3-[3-[2-ethyl-5-hydroxy-4-(4-fluorophenyl)phenoxy]propoxy]phenoxy]benzoic acid disodium salt hydrate

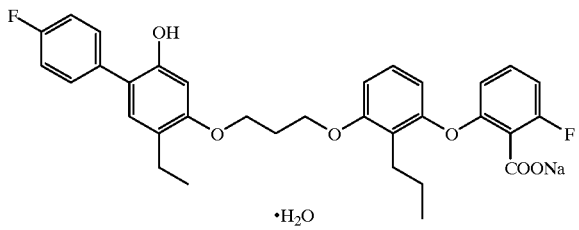

A. Preparation of 2-fluoro-6-[2-propyl-3-[3-[4-bromo-2-ethyl-5-(phenylmethoxy)phenoxy]propoxy]phenoxy] benzoic acid methyl ester 2-Fluoro-6-(3-hydroxy-2-propylphenoxy)benzoic acid methyl ester (1.84 g, 4.80 mmol) was alkylated with 2-benzyloxy-1-bromo-5-ethyl-4-(3-chloro-1-propyloxy) benzene to provide crude product as an oil. Silica gel chromatography provided 2.05 g (66%) of the purified title intermediate as a colorless oil: NMR (CDCl$_3$) 7.49 (d, J=7.1 Hz, 2H), 7.20–7.45 (m, 5H), 7.14 (t, J=8.2 Hz, 1H), 6.82 (t, J=8.5 Hz, 1H), 6.73 (d, J=8.3 Hz, 1H), 6.60 (d, J=8.4 Hz, 1H), 6.53 (s, 1H), 6.52 (d, J=8.5 Hz, 1H), 5.13 (s, 2H), 4.20 (t, J=6.0 Hz, 2H), 4.13 (t, J=6.0 Hz, 2H), 3.92 (s, 3H), 2.58 (m, 4H), 2.30 (quintet, J=6.0 Hz, 2H), 1.51 (hextet, J=7.6 Hz, 2H), 1.16 (t, J=7.9 Hz, 3H), 0.90 (t, J=7.3 Hz, 3H).

B. Preparation of 2-fluoro-6-[2-propyl-3-13-[2-ethyl-5-hydroxy-4-(4-fluorophenyl)phenoxy)propoxy]phenoxy] benzoic acid disodium salt hydrate To a solution of 2-fluoro-6-[2-propyl-3-[3-[4-bromo-2-ethyl-5-(phenylmethoxy)phenoxy]propoxy]phenoxy] benzoic acid methyl ester (1.77 g, 2.72 mmol) in benzene (12 mL) was added tetrakis(triphenylphosphine)palladium (0) (0.33 g, 0.30 mmol) and 2.0 M aqueous sodium carbonate (4 mL). To this mixture was added a solution of 4-fluorophenylboronic acid (4.10 g, 8.16 mmol) in ethanol (5 mL). The resulting mixture was refluxed for 4 hours then cooled to room temperature. The mixture was diluted with ethyl acetate and shaken. The organic layer was washed once with water and once with 1N aqueous sodium hydroxide, dried over sodium sulfate, filtered, and concentrated in vacuo to provide an oil. The product was de-benzylated, hydrolysed, salified, and purified to provide 403 mg (25%) of the desired title product as a fluffy white solid: NMR (DMSO-d$_6$) 9.83 (bs, 1H), 7.50 (m, 2H), 6.96–7.16 (m, 4H), 6.96 (s, 1H), 6.74 (t, J=8.4 Hz, 2H), 6.57 (s, 1H), 6.40 (d, J =8.3 Hz, 1H), 6.35 (d, J=8.3 Hz, 1H), 4.16 (t, J=5.7 Hz, 2H), 4.05 (t, J=5.5 Hz, 2H), 2.40–2.58 (m, 4H), 2.18 (quintet, J=4.1 Hz, 2H), 1.41 (hextet, J=7.4 Hz, 2H), 1.07 (t, J=7.5 Hz, 3H), 0.80 (t, J=7.3 Hz, 3H); MS-FAB m/e 586 (p+1, 35), 585 (p, 100), 562 (33), 313 (30). IR (CHCl$_3$, cm$^{-1}$) 3300 (b), 2967, 1616, 1455, 1398, 1115.

Analysis for $C_{33}H_{31}O_6F_2NaH_2O$: Calc: C, 65.77; H, 5.52; Found: C, 65.81; H, 5.41.

EXAMPLE 7

4-Fluoro-2-[2-propyl-3-[3-[2-ethyl-5-hydroxy-4-(4-fluorophenyl)phenoxy]propoxy]phenoxy]benzoic acid

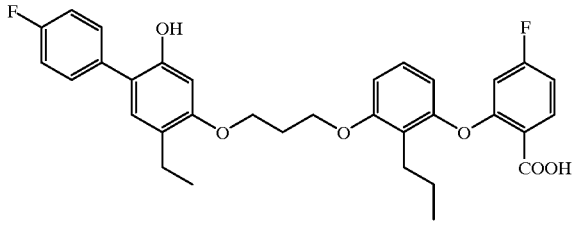

A. Preparation of 4-fluoro-2-(3-hydroxy-2-propyl-phenoxy)benzoic acid methyl ester To a solution of 2-propylresorcinol (10.0 g, 65.7 mmol) in pyridine (120 mL) was added potassium tert-butoxide (7.00 g, 62.5 mmol) at room temperature with stirring. To this was added a mixture of methyl 2-bromo-4-fluorobenzoate (7.60 g, 32.6 mmol) and copper(I) iodide (12.5 g, 65.7 mmol) in pyridine (120 mL). The resulting mixture was gently refluxed for 4 hours. The reaction was cooled to room temperature and stirred for 18 hours. The mixture was concentrated in vacuo and the resulting material dissolved in ethyl ether. The solution was washed once with 5N aqueous hydrochloric acid. The aqueous layer was extracted once with fresh ethyl ether and the combined organic layers were washed twice with 5N aqueous ammonium hydroxide. The organic layer was washed once with a saturated sodium chloride solution, dried over sodium sulfate, filtered, and concentrated in vacuo. Silica gel chromatography of the resulting residue provided 1.45 g (15%) of the desired intermediate product as a light tan solid: mp 92–94° C.; NMR (CDCl$_3$) 7.95 (m, 1H), 7.04 (t, J=9.5 Hz, 1H), 6.79 (t, J=9 Hz, 1H), 6.65 (d, J=9.5 Hz, 1H), 6.50 (m, 2H), 5.25 (bs, 1H, —OH), 3.88 (s, 3H), 2.60 (t, J=8.7 Hz, 2H), 1.55 (hextet, J=7.8 Hz, 2H), 0.92 (t, J=7.8 Hz, 3H); MS-FD m/e 305 (p+1, 40), 304 (p, 100); IR.

Analysis for $C_{17}H_{17}O_4F$: Calc: C, 67.10; H, 5.63; Found: C, 67.32; H, 5.78.

B. Preparation of 4-fluoro-2-[2-propyl-3-[3-[4-(4-fluorophenyl)-2-ethyl-5-(phenylmethoxy)phenoxy] propoxy]phenoxy]benzoic acid methyl ester 4-Fluoro-6-(3-hydroxy-2-propylphenoxy)benzoic acid methyl ester (0.534 g, 1.75 mmol) was alkylated with 2-benzyloxy-1-(4-fluorophenyl)-5-ethyl-4-(3-chloro-1-propyloxy)benzene to provide crude product as an oil. Purification via silica gel chromatography provided 640 mg (55%) of the desired title intermediate as a white crystalline solid: mp 77–78° C.; NMR (CDCl$_3$) 7.95 (t, J=7.8 Hz, 1H), 7.53 (m, 2H), 7.32 (m, 4H), 7.03–7.20 (m, 3H), 6.77 (m, 2H), 6.62 (s, 1H), 6.55 (d, J=8 Hz, 1H), 6.50 (d, J=9 Hz, 1H), 5.05 (s, 2H), 4.25 (m, 4H), 3.89 (s, 3H), 2.65 (m, 4H), 2.34 (quintet, J=6 Hz, 4H), 1.55 (hextet, J=6 Hz, 2H), 1.22 (t, J=7 Hz, 3H), 0.92 (t, J =7 Hz, 3H); MS-FD m/e 666 (p); IR (CHCl$_3$, cm$^{-1}$) 2960, 1730, 1600, 1499, 1461, 1268, 1110.

Analysis for $C_{44}H_{40}O_6F_2$: Calc: C, 73.86; H, 6.05; Found: C, 73.17; H, 6.44.

C. Preparation of 4-fluoro-2-[2-propyl-3-[3-[4-(4-fluorophenyl)-2-ethyl-5-hydroxyphenoxy)propoxy] phenoxy]benzoic acid methyl ester 4-Fluoro-2-[2-propyl-3-[3-[4-(4-fluorophenyl)-2-ethyl-5-(phenylmethoxy)phenoxy)propoxy]phenoxy]benzoic acid methyl ester (590 mg) was dissolved in ethyl acetate (25 mL) containing 10% palladium on carbon (118 mg) and hydrogenated at 2 atmospheres for 18 hours. The mixture was filtered through Celite® and concentrated in vacuo to provide an oil. Purification of the crude material via silica gel chromatography provided 400 mg (79%) of the title intermediate as a glass: NMR (CDCl$_3$) 7.97 (t, J=7.8 Hz, 1H), 7.44 (m, 2H), 7.17 (m, 3H), 7.03 (s, 1H), 6.79 (m, 2H), 6.45–6.63 (m, 3H), 5.38 (bs, 1H, —OH), 4.22 (m, 4H), 3.92 (s, 3H), 2.65 (m, 4H), 2.35 (quintet, J=5 Hz, 2H), 1.57 (hextet, J=7 Hz, 2H), 1.24 (t, J=7.8 Hz, 3H), 0.95 (t, J=7.8 Hz, 3H); MS-FD m/e 578 (p+2, 50), 577 (p +1, 90), 576 (p, 100); IR (CHCl$_3$, cm$^{-1}$) 3563 (b), 2965, 1722, 1604, 1585, 1497, 1461, 1267, 1251, 1152, 1110.

Analysis for $C_{34}H_{34}O_6F_2$: Calc: C, 70.82; H, 5.94; Found: C, 71.12; H, 5.96.

7.10–7.30 (m, 3H), 7.97 (s, 1H), 6.84 (m, 2H), 6.63 (d, J=6.8 Hz, 1H), 6.52 (s, 1H), 6.41 (d, J=9 Hz, 1H), 5.10 (bs, 1H, —OH), 4.23 (m, 4H), 2.57 (m, 4H), 2.34 (quintet, J=5 Hz, 2H), 1.50 (hextet, J=6 Hz, 2H), 1.17 (t, J=7.8 Hz, 3H), 0.88 (t, =7.8 Hz, 3H); MS-FD m/e 564 (p+2, 30), 562 (p, 100); IR (CHCl$_3$, cm$^{-1}$) 3379 (b), 2963, 1699, 1607, 1500, 1268, 1247, 1146, 1110, 839.

Analysis for $C_{33}H_{32}O_6F_2$: Calc: C, 70.45; H, 5.73; Found: C, 70.15; H, 5.81.

EXAMPLE 8

2-[2-Propyl-3-[5-[2-ethyl-5-hydroxy-4-(4-fluorophenyl)phenoxy]pentoxy]phenoxy]benzoic acid

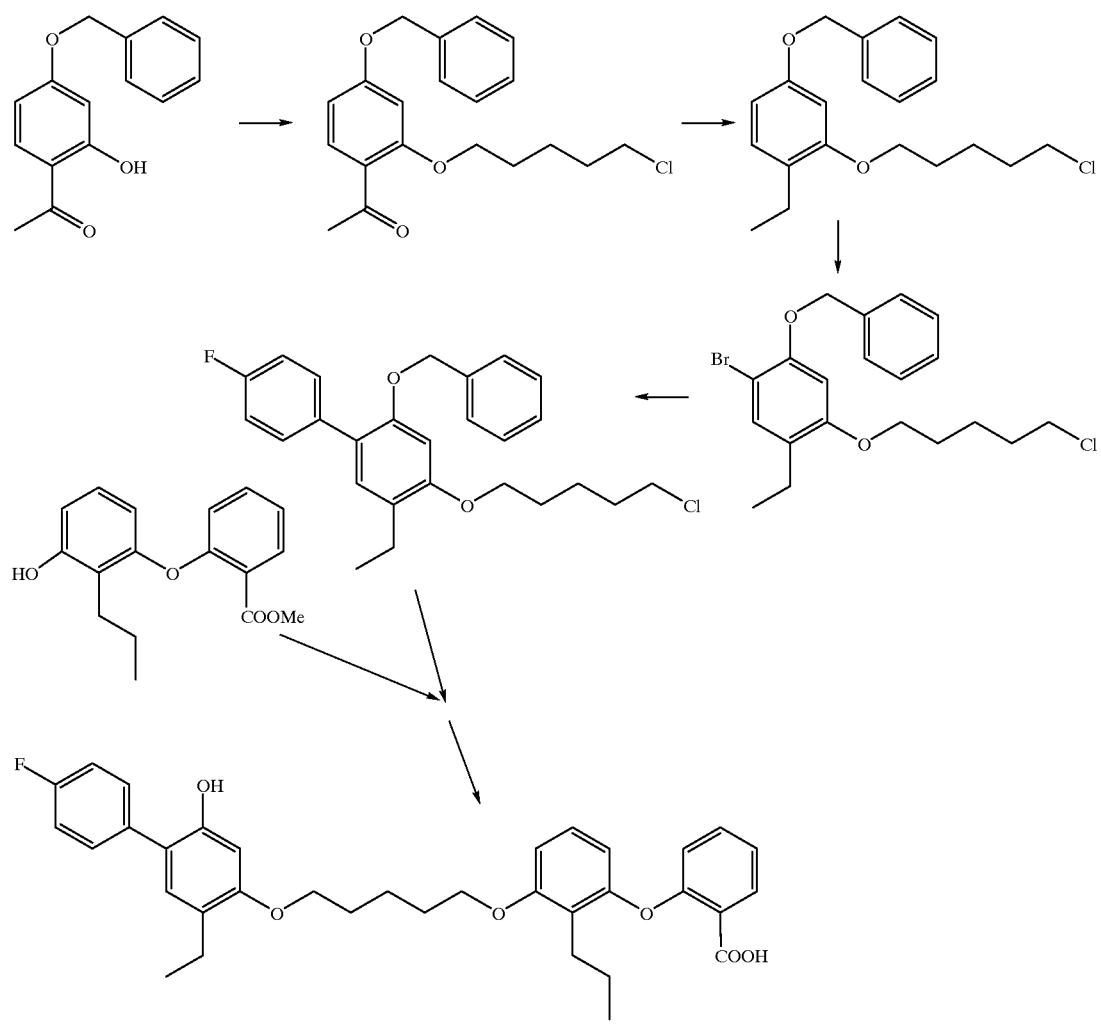

D. Preparation of 4-fluoro-2-[2-propyl-3-[3-[2-ethyl-5-hydroxy-4-(4-fluorophenyl)phenoxy]propoxy]phenoxy]benzoic acid 4-Fluoro-2-[2-propyl-3-[3-[4-(4-fluorophenyl)-2-ethyl-5-hydroxyphenoxy]propoxy]phenoxy]benzoic acid methyl ester (350 mg) was hydrolyzed to provide 310 mg (91%) of the desired title product as a white solid: mp 62–64° C.; NMR (CDCl$_3$) 8.21 (t, J=7.8 Hz, 1H), 7.35 (m, 2H), A. Preparation of 2-(5-chloropentoxy)-4-(phenylmethoxy)acetophenone A mixture of 2-hydroxy-4-(phenylmethoxy)acetophenone (15.5 g, 64.0 mmol), potassium carbonate (8.83 g, 64.0 mmol), and dimethylsulfoxide (15 mL) in 2-butanone (145 mL) was stirred at room temperature for 30 minutes. 1-Bromo-5-chloropentane (11.9 g, 64.0 mmol) was added and the resulting mixture heated at reflux for 18 hours. The reaction mixture was cooled, diluted with water, and extracted with ethyl acetate. The organic layer was washed once with a saturated sodium chloride solution, dried over sodium sulfate, filtered, and concentrated in vacuo to provide a waxy solid. Purification via silica gel chromatography (ethyl acetate/hexane) provided 16.1 g (73%) of the title intermediate as a white solid: mp 76–77° C.; NMR (CDCl$_3$) 7.85 (d, J=8.7 Hz, 1H), 7.43 (m, 5H), 6.59 (d, J=8.5 Hz, 1H), 6.53 (s, 1H), 5.11 (s, 2H), 4.05 (t, J =6 Hz, 2H), 3.61 (t, J=6 Hz, 2H), 2.60 (s, 3H), 1.90 (m, 4H), 1.69 (m, 2H); MS-FD m/e 348 (p+2, 65), 346 (p, 100); IR (CHCl$_3$, cm$^{-1}$) 3025, 1662, 1598, 1268, 1184, 1139, 1027.

B. Preparation of 2-(5-chloropentoxy)-4-(phenylmethoxy)ethylbenzene

To a solution of 2-(5-chloropentoxy)-4-(phenylmethoxy)-acetophenone (15.0 g, 43.2 mmol) in trifluoroacetic acid (33.3 mL) at 0° C. was added triethylsilane (11.0 g, 95.1 mmol) dropwise. The resulting mixture was stirred at 0° C. for 2.5 hours then treated with excess saturated sodium bicarbonate solution. The mixture was extracted with ether. The organic layer was washed once with a saturated sodium chloride solution, dried over sodium sulfate, filtered, and concentrated in vacuo to reveal a yellow oil. Purification via silica gel chromatography (ethyl acetate/hexane) provided 10.45 g (73%) of the title intermediate as a faint yellow oil: NMR (CDCl$_3$) 7.20–7.55 (m, 5H), 7.08 (d, J=9.7 Hz, 1H), 6.53 (s, 1H), 6.51 (d, J=8.7 Hz, 1H), 5.05 (s, 2H), 3.95 (t, J =6.8 Hz, 2H), 3.60 (t, J=6.8 Hz, 2H), 2.59 (q, J=7.8 Hz, 2H), 1.75–1.95 (m, 4H), 1.69 (quintet, J=6 Hz), 1.18 (t, J=7.8 Hz, 3H); MS-FD m/e ; IR (CHCl$_3$, cm$^{-1}$) 2937, 1613, 1587, 1505, 1289, 1258, 1172, 1132, 1028.

Analysis for $C_{20}H_{25}O_2Cl$: Calc: C, 72.12; H, 7.57; Found: C, 71.24; H, 7.64.

C. Preparation of 3-bromo-6-(5-chloropentoxy)-4-(phenylmethoxy)ethylbenzene

A mixture of 2-(5-chloropentoxy)-4-(phenylmethoxy)-ethylbenzene (10.0 g, 31.0 mmol) and N-bromosuccinimide (5.35 g, 30.1 mmol) in carbon tetrachloride (100 mL) was warmed slightly for 2 hours, then stirred at room temperature for 18 hours. The mixture was washed sequentially with water, 1N aqueous sodium thiosulfate solution, and saturated sodium chloride solution. The organic layer was dried over sodium sulfate, filtered, and concentrated in vacuo to provide a white solid. Recrystallization from hexane provided 10.0 g (81%) of the desired title intermediate as a white crystalline solid: mp 54–55° C.; NMR (CDCl$_3$) 7.50 (m, 2H), 7.25–7.48 (m, 4H), 6.48 (s, 1H), 5.15 (s, 2H), 3.91 (t, J=6 Hz, 2H), 3.58 (t, J=6 Hz, 2H), 2.55 (q, J=7 Hz, 2H), 1.85 (m, 4H), 1.65 (m, 2H), 1.16 (t, J=7.8 Hz, 3H); MS-FD m/e 414 (p+2, 25), 412 (p, 100), 410 (p−2, 85); IR (CHCl$_3$, cm$^{-1}$) 2950, 1602, 1501, 1450, 1370, 1300, 1163.

Analysis for $C_{20}H_{24}O_2BrCl$: Calc: C, 58.34; H, 5.87; Found: C, 58.31; H, 6.04.

D. Preparation of 6-(5-chloropentoxy)-2-(4-fluorophenyl)-4-(phenylmethoxy)ethylbenzene 3-Bromo-6-(5-chloropentoxy)-4-(phenylmethoxy)-ethylbenzene (8.80 g, 26.4 mmol) was coupled to 4-fluorophenyl-boronic acid. Purification via silica gel chromatography (ethyl acetate/hexane) followed by recrystallization from hexane provided 7.04 g (77%) of the intermediate title product as a white solid: mp 55–56° C.; NMR (CDCl$_3$) 7.54 (m, 2H), 7.33 (m, 5H), 7.11 (m, 3H), 6.59 (s, 1H), 5.07 (s, 2H), 3.99 (t, J=6 Hz, 2H), 3.62 (t, J=6 Hz, 2H), 2.65 (q, J=8 Hz, 2H), 1.90 (m, 4H), 1.70 (m, 2H), 1.14 (t, J=8 Hz, 3H); IR (CHCl$_3$, cm$^{-1}$) 2938, 1613, 1497, 1143, 1027.

Analysis for $C_{26}H_{28}O_2ClF$: Calc: C, 73.14; H, 6.61; Found: C, 72.91; H, 6.69.

E. Preparation of 2-[2-propyl-3-[5-[2-ethyl-4-(4-fluorophenyl)-5-(phenylmethoxy)phenoxy]pentoxy]phenoxy]benzoic acid methyl ester 2-(3-Hydroxy-2-propylphenoxy)benzoic acid methyl ester (2.00 g, 6.99 mmol) was alkylated with 6-(5-chloropentoxy)-2-(4-fluorophenyl)-4-(phenylmethoxy) ethylbenzene to provide crude product as an oil. Purification via silica gel chromatography (ethyl acetate/hexane) provided 3.90 g (83%) of title intermediate as a colorless oil: NMR (CDCl$_3$) 7.94 (d, J=8 Hz, 1H), 7.55 (m, 2H), 7.35 (m, 6H), 7.11 (m, 5H), 6.85 (d, J=9 Hz, 1H), 6.70 (d, J=9 Hz, 1H), 6.60 (s, 1H), 6.48 (d, J=9 Hz, 1H), 5.07 (s, 2H), 4.08 (t, J=5 Hz, 2H), 4.03 (t, J=5 Hz, 2H), 3.89 (s, 3H), 2.70 (m, 4H), 1.95 (m, 4H), 1.76 (m, 2H), 1.62 (m, 2H), 1.24 (t, J=7 Hz, 3H), 0.95 (t, J=7 Hz, 3H); MS-FD m/e 677 (p+1, 65), 676 (p, 100); IR (CHCl$_3$, cm$^{-1}$) 2965, 1740, 1604, 1497, 1461, 1453, 1306, 1111.

Analysis for $C_{42}H_{45}O_6F$: Calc: C, 76.31; H, 6.70; Found: C, 76.24; H, 6.83.

F. Preparation of 2-[2-propyl-3-[5-[2-ethyl-5-hydroxy-4-(4-fluorophenyl)phenoxy]pentoxy]phenoxy]benzoic acid 2-[2-Propyl-3-[5-[2-ethyl-4-(4-fluorophenyl)-5-(phenylmethoxy)phenoxy]pentoxy]phenoxy]benzoic acid methyl ester (3.60 g, 5.32 mmol) was submitted to de-benzylation and hydrolysis. The resulting product was isolated via vacuum filtration as a white crystalline solid: mp 65° C. (dec); NMR (CDCl$_3$) 8.25 (dd, J=7.9, 1.7 Hz, 1H), 7.44 (m, 3H), 7.18 (m, 4H), 6.97 (s, 1H), 6.80 (d, J=8.2 Hz, 1H), 6.75 (d, J=8.5 Hz, 1H), 6.65 (d, J=8.1 Hz, 1H), 6.54 (s, 1H), 5.15 (bs, 1H, —OH), 4.10 (t, J=6.1 Hz, 2H), 4.05 (t, J=5.6 Hz, 2H), 2.61 (m, 4H), 1.93 (m, 4H), 1.75 (m, 2H), 1.54 (hextet, J=7.4 Hz, 2H), 1.18 (t, J=7.4 Hz, 3H), 0.89 (t, J=7.3 Hz, 3H); MS-FD m/e 572 (p); IR (CHCl$_3$, cm$^{-1}$) 3350 (b), 2965, 1739, 1605, 1496, 1455, 1238, 1108.

Analysis for $C_{35}H_{37}O_6F$: Calc: C, 73.41; H, 6.51; Found: C, 73.13; H, 6.59.

EXAMPLE 9

2-(2-Propyl-3-[4-[2-ethyl-5-hydroxy-4-(4-fluorophenyl)-phenoxylbutoxy]phenoxy]benzoic acid sesquihydrate

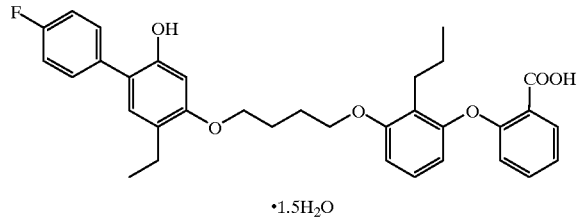

•1.5H$_2$O

A. Preparation of 2-(4-chlorobutoxy)-4-(phenylmethoxy)acetophenone

2-Hydroxy-4-(phenylmethoxy)acetophenone (9.20 g, 37.9 mmol) was alkylated with 1-bromo-4-chlorobutane. The crude material was purified via silica gel chromatography (ethyl acetate/hexane) to provide 7.70 g (61%) of the desired title product as a white solid: mp 58–60° C.; NMR (CDCl$_3$) 7.83 (d, J=9 Hz, 1H), 7.33–7.47 (m, 5H), 6.59 (dd, J=9, 2 Hz, 1H), 6.53 (d, J=2 Hz, 1H), 5.10 (s, 2H), 4.05 (t, J =5 Hz, 2H), 3.62 (t, J=5 Hz, 2H), 2.57 (s, 3H), 2.02 (m, 4H); MS-FD m/e 334 (p+1, 50), 333 (p, 28), 332 (p−1, 100); IR (CHCl$_3$, cm$^{-1}$) 3013, 1663, 1599, 1267, 1184, 1027.

Analysis for $C_{19}H_{21}O_3Cl$: Calc: C, 68.57; H, 6.36; Found: C, 68.77; H, 6.60.

B. Preparation of 2-(4-chlorobutoxy)-4-(phenyl-methoxy)ethylbenzene 2-(4-Chlorobutoxy)-4-(phenylmethoxy)-acetophenone (3.50 g, 10.5 mmol) was reduced. Purification via silica gel chromatography (ethyl acetate/hexane) provided 2.60 g (79%) of the desired title intermediate as a colorless oil: NMR (CDCl$_3$) 7.13–7.55 (m, 5H), 7.08 (d, J=8.9 Hz, 1H), 6.54 (m, 2H), 5.07 (s, 2H), 3.99 (d, J=5.7 Hz, 2H), 3.65 (t, J=6.0 Hz, 2H), 2.65 (q, J=7.5 Hz, 2H), 2.00 (m, 4H), 1.22 (t, J=7.5 Hz, 3H); MS-FD m/e; IR (CHCl$_3$, cm$^{-1}$) 2966, 1613, 1506, 1289, 1171, 1132, 1028.

Analysis for C$_{19}$H$_{23}$O$_2$Cl: Calc: C, 71.57; H, 7.27; Found: C, 71.78; H, 7.40.

C. Preparation of 3-bromo-6-(4-chlorobutoxy)-4-(phenylmethoxy)ethylbenzene 2-(4-Chlorobutoxy)-4-(phenylmethoxy)ethylbenzene (2.50 g, 7.84 mmol) was brominated. Recrystallization of the crude product from hexane provided 2.52 g (81%) of the desired title product: mp 65–66° C.; NMR (CDCl$_3$) 7.50 (d, J =8 Hz, 2H), 7.34–7.48 (m, 3H), 7.32 (s, 1H), 6.49 (s, 1H), 5.15 (s, 2H), 3.92 (t, J=5.6 Hz, 2H), 3.64 (t, J=5.9 Hz, 2H), 2.55 (q, J=7.5 Hz, 2H), 1.97 (m, 4H), 1.15 (t, J =7.5 Hz, 3H); MS-FD m/e 398 (p, 100), 396 (p–2, 70); IR (CHCl$_3$, cm$^{-1}$) 2967, 1602, 1501, 1455, 1389, 1285, 1163, 1060.

Analysis for C$_{19}$H$_{22}$O$_2$BrCl: Calc: C, 57.38; H, 5.57; Found: C, 57.27; H, 5.62.

D. Preparation of 6-(4-chlorobutoxy)-2-(4-fluorophenyl)-4-(phenylmethoxy)ethylbenzene 3-Bromo-6-(4-chlorobutoxy)-4-(phenylmethoxy)-ethylbenzene (2.30 g, 26.4 mmol) was coupled to 4-fluorophenylboronic acid. Purification via silica gel chromatography (ethyl acetate/hexane) followed by trituration with methanol provided 2.07 g (87%) of the titled intermediate product as a white solid: mp 48–49° C.; NMR (CDCl$_3$) 7.55 (m, 2H), 7.35 (m, 5H), 7.12 (m, 3H), 6.59 (s, 1H), 5.08 (s, 2H), 4.03 (t, J=5.3 Hz, 2H), 3.68 (t, J =5.3 Hz, 2H), 2.67 (q, J=7.5 Hz, 2H), 2.02 (m, 4H), 1.24 (t, J=7.5 Hz, 3H); MS-FD m/e 412 (p); IR.

Analysis for C$_{25}$H$_{26}$O$_2$C$_1$F: Calc: C, 72.72; H, 6.35; Found: C, 72.59; H, 6.46.

E. Preparation of 2-[2-propyl-3-[4-[2-ethyl-4-(4-fluorophenyl)-5-(phenylmethoxy)phenoxy]butoxy]phenoxy]benzoic acid methyl ester 2-(3-Hydroxy-2-propylphenoxy)benzoic acid methyl ester (1.40 g, 4.84 mmol) was alkylated with 6-(4-chlorobutoxy)-2-(4-fluorophenyl)-4-(phenylmethoxy)ethylbenzene to provide crude product as an oil. Purification via silica gel chromatography (ethyl acetate/hexane) provided 2.40 g (75%) of the title intermediate as a colorless oil: NMR (CDCl$_3$) 7.93 (dd, J=6.2, 1.7 Hz, 1H), 7.54 (m, 2H), 7.25–7.45 (m, 6H), 7.13 (m, 5H), 6.88 (d, J=8.8 Hz, 1H), 6.70 (d, J=8.8 Hz, 1H), 6.63 (s, 1H), 6.50 (d, J=8.3 Hz, 1H), 5.07 (s, 2H), 4.12 (m, 4H), 3.89 (s, 3H), 2.68 (m, 4H), 2.09 (m, 4H), 1.63 (hextet, J=7.4 Hz, 2H), 1.15 (t, J=7.4 Hz, 3H), 0.97 (t, J=7.4 Hz, 3H); MS-FD m/e 663 (p+1, 35), 662 (p, 100); IR (CHCl$_3$, cm$^{-1}$) 3470, 2950, 1760, 1740, 1461, 1305, 1135, 1071.

Analysis for C$_{42}$H$_{43}$O$_6$F: Calc: C, 76.11; H, 6.54; Found: C, 76.36; H, 6.65.

F. Preparation of 2-[2-propyl-3-[4-[2-ethyl-5-hydroxy-4-(4-fluorophenyl)phenoxy]butoxy]phenoxy]benzoic acid sesquihydrate 2-[2-Propyl-3-[4-[2-ethyl-4-(4-fluorophenyl)-5-(phenylmethoxy)phenoxylbutoxy]phenoxy]benzoic acid methyl ester (2.20 g, 3.32 mmol) was submitted to de-benzylation and hydrolysis. This procedure provided 1.00 g (85%) of the title product as a white solid: mp 65–68° C.; NMR (CDCl$_3$) 8.26 (dd, J=6.0, 1.8 Hz, 1H), 7.43 (m, 3H), 7.12–7.29 (m, 4H), 6.99 (s, 1H), 6.81 (d, J=8 Hz, 1H), 6.75 (d, J=8.2 Hz, 1H), 6.65 (d, J=8 Hz, 1H), 6.53 (s, 1H), 5.08 (bs, 1H, —OH), 4.12 (m, 4H), 2.63 (m, 4H), 2.08 (m, 4H), 1.55 (hextet, J=7.4 Hz, 2H), 1.20 (t, J=7.4 Hz, 3H), 0.90 (t, J=7.4 Hz, 3H); MS-FD m/e 559 (p+1, 57), 558 (p, 100); IR (CHCl$_3$, cm$^{-1}$) 3350 (b), 2950, 1739, 1625, 1496, 1455, 1237, 1108.

Analysis for C$_{34}$H$_{35}$O$_6$F.1.5 H$_2$O: Calc: C, 69.73; H, 6.43; Found: C, 69.74; H, 6.54.

EXAMPLE 10

2-[2-(2-Methylpropyl)-3-[3-(2-ethyl-5-hydroxy-4-(4-fluorophenyl)phenoxy]propoxy]phenoxy]benzoic acid

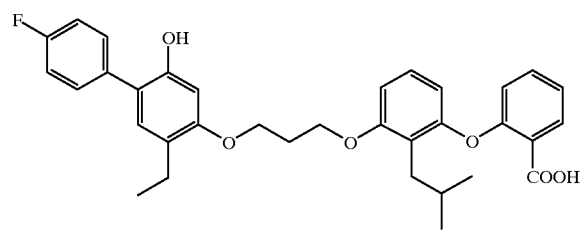

A. Preparation of 2-(2-methylpropyl)-1,3-dimethoxybenzene

To a solution of 1,3-dimethoxybenzene (38.0 g, 272 mmol) in tetrahydrofuran (380 mL) at 0° C. was added a 1.6M solution of butyllithium in hexane (188 mL, 299 mmol). The resulting mixture was stirred at 0° C. for 2 hours. 1-Iodo-2-methylpropane (50.0 g, 272 mmol) was added and the reaction mixture warmed to room temperature, then refluxed for 36 hours. The mixture was cooled to room temperature, diluted with saturated ammonium chloride solution, and extracted twice with ethyl acetate. The organic layer was dried over sodium sulfate, filtered, and concentrated in vacuo. Purification via silica chromatography (ethyl acetate/hexane) provided 13.8 g (26%) of title intermediate product as a colorless oil: NMR (CDCl$_3$) 7.22 (t, J=9 Hz, 1H), 6.33 (d, J=10 Hz, 2H), 3.89 (s, 6H), 2.66 (d, J=9 Hz, 2H), 2.03 (heptet, J=8 Hz, 1H), 1.00 (d, J=8 Hz, 6H); IR (CHCl$_3$, cm$^{-1}$) 2959, 1593, 1474, 1261, 1133, 1075.

B. Preparation of 2-(2-methylpropyl)-1,3-dihydroxybenzene 2-(2-Methylpropyl)-1,3-dimethoxybenzene (18.0 g, 92.8 mmol) was melted with pyridinium hydrochloride (90 g) and stirred at 180° C. for 8 hours. The mixture was cooled to room temperature, diluted with water, and extracted twice with ethyl acetate. The organic phase was washed with dilute aqueous hydrochloric acid, dried over sodium sulfate, filtered and concentrated in vacuo. Purification via silica gel chromatography (ether/hexane) provided 15.0 g (98%) of title intermediate as a light yellow oil: NMR (CDCl$_3$) 6.97 (t, J=9 Hz, 1H), 6.43 (d, J=10 Hz, 2H), 5.68 (s, 2H, —OH), 2.59 (d, J=9 Hz, 2H), 2.03 (heptet,
J=8 Hz, 1H), 1.00 (d, J=8 Hz, 6H); MS-FD m/e 166 (p); IR (CHCl$_3$, cm$^{-1}$) 3603, 3349 (b), 2959, 1601, 1466, 1298, 1104, 987.

Analysis for C$_{10}$H$_{14}$O$_2$: Calc: C, 72.26; H, 8.49; Found: C, 72.37; H, 8.75.

C. Preparation of 2-[3-hydroxy-2-(2-methylpropyl)-phenoxy]benzoic acid methyl ester 2-(2-Methylpropyl)-1,3-dihydroxybenzene (14.5 g, 87.3 mmol) was submitted to Ullmann coupling conditions with methyl 2-iodobenzoate. Purification of the crude product via silica gel chromatography (ether/hexane) provided 3.11 g (12%) of the desired title intermediate as a light yellow oil: NMR (CDCl$_3$) 7.91 (d, J=8 Hz, 1H), 7.23 (t, J=8 Hz, 1H), 7.16 (t, J=8 Hz, 1H), 6.99 (t, J=8 Hz, 1H), 6.86 (d, J=9 Hz, 1H), 6.63 (d, J=9 Hz, 1H), 6.39 (d, J =9 Hz, 1H), 5.42 (bs, 1H, —OH), 3.84 (s, 3H), 2.58 (d, J=9 Hz, 2H), 2.08 (heptet, J=8 Hz, 1H), 0.99 (d, J=8 Hz, 6H); MS-FD m/e 300 (p); IR (CHCl$_3$, cm$^{-1}$) 3625, 3360 (b), 2950, 1718, 1602, 1453, 1306, 1235, 1107, 910.

Analysis for $C_{18}H_{20}O_4$: Calc: C, 71.98; H, 6.71; Found: C, 72.19; H, 6.86.

D. Preparation of 2-[2-(2-methylpropyl)-3-[3-[2-ethyl-5-(phenylmethoxy)-4-(4-fluorophenyl)phenoxy]propoxy]phenoxy]benzoic acid methyl ester 2-[3-Hydroxy-2-(2-methylpropyl)phenoxy]benzoic acid methyl ester (750 mg, 2.51 mmol) was alkylated with 2-benzyloxy-1-(4-fluorophenyl)-5-ethyl-4-(3-chloro-1-propyloxy)benzene to provide crude product as an oil. Purification via silica gel chromatography (ether/hexane) provided 620 mg (35%) of title intermediate product as an off-white solid: mp 82–84° C.; NMR (CDCl$_3$) 7.99 (d, J=8 Hz, 1H), 7.62 (t, J=7 Hz, 2H), 7.38 (m, 6H), 7.18 (m, 5H), 6.90 (d, J=9H, 1H), 6.78 (d, J=9 Hz, 1H), 6.71 (s, 1H), 6.53 (d, J=9 Hz, 1H), 5.09 (s, 2H), 4.27 (m, 4H), 3.91 (s, 3H), 2.70 (m, 4H), 2.39 (quintet, J=8 Hz, 2H), 2.10 (heptet, J=8 Hz, 1H), 1.30 (t, J=9 Hz, 3H), 1.00 (d, J=8 Hz, 6H); MS-FD m/e 663 (p+1, 42), 662 (p, 100); IR (KBr, cm$^{-1}$) 3425 (b), 2959, 2864, 1733, 1604, 1580, 1500, 1447, 1246, 1080, 837.

Analysis for $C_{42}H_{43}O_6F$: Calc: C, 76.11; H, 6.54; Found: C, 76.20; H, 6.83.

E. Preparation of 2-[2-(2-methylpropyl)-3-[3-[2-ethyl-5-hydroxy-4-(4-fluorophenyl)phenoxy]propoxy]phenoxy]benzoic acid 2-[2-(2-Methylpropyl)-3-[3-[2-ethyl-5-(phenylmethoxy)-4-(4-fluorophenyl)phenoxy]propoxy]phenoxy]benzoic acid methyl ester (600 mg, 0.906 mmol) was submitted to de-benzylation conditions. Hydrolysis of the resulting ester provided 250 mg (57%) of title product as an off-white solid: mp 48–49° C.; NMR (CDCl$_3$) 8.25 (d, J=9 Hz, 1H), 7.44 (m, 3H), 7.20 (m, 4H), 7.05 (S, 1H), 6.85 (d, J=9 Hz, 1H), 6.76 (d, J=9 Hz, 1H), 6.64 (d, J=9 Hz, 1H), 6.59 (s, 1H), 5.32 (bs, 1H, —OH), 4.28 (m, 4H), 2.63 (q, J =8 Hz, 2H), 2.52 (d, J=8 Hz, 2H), 2.38 (quintet, J=8 Hz, 2H), 1.96 (heptet, J=8 Hz, 1H), 1.23 (t, J=9 Hz, 3H), 0.98 (d, J=8 Hz, 6H); MS-FD m/e 559 (p+1, 39), 558 (p, 100); IR (KBr, cm$^{-1}$) 3350 (b), 2958, 1699, 1604, 1457, 1222, 1112, 1062, 838, 756.

Analysis for $C_{34}H_{35}O_6F$: Calc: C, 73.10; H, 6.31; Found: C, 73.32; H, 6.50.

EXAMPLE 11

2-[2-Butyl-3-[3-[2-ethyl-5-hydroxy-4-(4-fluorophenyl)phenoxy]propoxy]phenoxy]benzoic acid hydrate

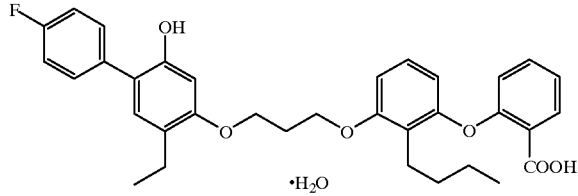

A. Preparation of 2-butyl-1,3-dimethoxybenzene 1,3-Dimethoxybenzene (15.0 g, 109 mmol) was alkylated with 1-iodobutane as described above for the preparation of Example 10(A) except that the final reaction mixture was not refluxed. Purification via silica gel chromatography (ethyl acetate/hexane) provided 15.0 g (71%) of the title intermediate product as a yellow oil: NMR (CDCl$_3$) 7.18 (t, J=8.2 Hz, 1H), 6.59 (d, J=9.7 Hz, 2H), 3.84 (s, 6H), 2.70 (t, J=8.7 Hz, 2H), 1.50 (hextet, J=6 Hz, 2H), 1.44 (quintet, J=6 Hz, 2H), 0.98 (t, J=8.2 Hz, 3H); MS-FD m/e 194 (p).

B. Preparation of 2-(3-hydroxy-2-butylphenoxy)-benzoic acid methyl ester

2-Butyl-1,3-dimethoxybenzene (14.98 g, 77.6 mmol) was de-methylated as described above for the preparation of Example 10(B) to provide 19 g crude product as a brown oil. A solution of 15 g of this material and potassium tert-butoxide (9.70 g, 86.5 mmol) in pyridine (150 mL) was added to a second solution of methyl 2-iodobenzoate (11.9 g, 180 mmol) and copper(I) iodide (17.3 g, 91.0 mmol) in pyridine (150 mL). The resulting mixture was refluxed for 36 hours. The mixture was cooled to room temperature, diluted with water, and extracted three times with diethyl ether. The combined ether fractions were filtered through a mat of Celite®, washed once with 5N aqueous hydrochloric acid, once with 2N aqueous sodium hydroxide, and filtered again through a mat of Celite®. The resulting solution was dried over magnesium sulfate, filtered, and evaporated in vacuo. Silica gel chromatography (ethyl acetate/hexane) provided 3.02 g (11%) of the title intermediate product as an orange oil: NMR (CDCl$_3$) 7.91 (d, J=8 Hz, 1H), 7.41 (t, J=8 Hz, 1H), 7.14 (t, J=8 Hz, 1H), 6.97 (t, J=9 Hz, 1H), 6.83 (d, J=8 Hz, 1H), 6.59 (d, J=8 Hz, 1H), 6.39 (d, J=8 Hz, 1H), 5.04 (bs, 1H, —OH), 3.83 (s, 3H), 2.66 (t, J=9 Hz, 2H), 1.54 (quintet, J=5 Hz, 2H), 1.35 (hextet, J=5 Hz, 2H), 0.91 (t, J=8 Hz, 3H); MS-EI m/e 300 (p, 34), 225 (100), 213 (42), 197 (53), 107 (38); IR (mull, cm$^{-1}$) 3410, 2926, 1709, 1600, 1463, 1234, 1107, 1090, 992.

Analysis for $C_{18}H_{20}O_4$: Calc: C, 71.98; H, 6.71; Found: C, 70.82; H, 6.67.

C. Preparation of 2-[2-butyl-3-[3-[2-ethyl-4-(4-fluorophenyl)-5-(phenylmethoxy)phenoxy]propoxy]phenoxy]benzoic acid methyl ester 2-(3-Hydroxy-2-butylphenoxy)benzoic acid methyl ester (700 mg, 1.76 mmol) was alkylated with 2-benzyloxy-1-(4-fluorophenyl)-5-ethyl-4-(3-chloro-1-propyloxy)benzene as described above for the preparation of Example 5(A) to provide crude product as an oil. Purification via silica gel chromatography (ethyl acetate/hexane) provided 700 mg (60%) of the title intermediate product as a yellow oil: NMR (CDCl$_3$) 7.91 (d, J=9 Hz, 1H), 7.58 (m, 2H), 7.38 (m, 6H), 7.18 (m, 5H), 6.88 (d, J=10 Hz, 1H), 6.76 (d, J=9 Hz, 1H), 6.68 (s, 1H), 6.47 (d, J=9 Hz, 1H), 5.09 (s, 2H), 4.25 (m, 4H), 3.91 (s, 3H), 2.72 (m, 4H), 2.40 (quintet, J=5 Hz, 2H), 1.60 (hextet, J=5 Hz, 2H), 1.38 (m, 2H), 1.24 (t, J=8 Hz, 3H), 0.99 (t, J=8 Hz, 3H); IR (CHCl$_3$, cm$^{-1}$) 3024, 1717, 1602, 1465, 1453, 1306, 1234, 1086, 1014.

Analysis for C$_{42}$H$_{43}$O$_6$F: Calc: C, 76.11; H, 6.54; Found: C, 75.82; H, 6.50.

D. Preparation of 2-[2-butyl-3-[3-[2-ethyl-5-hydroxy-4-(4-fluorophenyl)phenoxy]propoxy]phenoxy]benzoic acid hydrate 2-[2-Butyl-3- 3-[2-ethyl-4-(4-fluorophenyl)-5-(phenylmethoxy)phenoxy]propoxy]phenoxy]benzoic acid methyl ester (690 mg, 1.04 mmol) was submitted to de-benzylation conditions as described above for the preparation of Example 7(C). Hydrolysis of the resulting ester provided 114 mg (30%) of the title product as an off-white solid: mp 62–64° C.; NMR (DMSO-d$_6$) 12.75 (bs, 1H, —COOH), 9.60 (bs, 1H, —OH), 7.69 (d, J=7.3 Hz, 1H), 7.50 (m, 2H), 7.35 (t, J=7.4 Hz, 1H), 7.00–7.18 (m, 4H), 6.96 (s, 1H), 6.69 (m, 2H), 6.56 (s, 1H), 6.31 (d, J=8.2 Hz, 1H), 4.17 (t, J=5.1 Hz, 2H), 4.09 (t, J=5.4 Hz, 2H), 2.58 (t, J=7.3 Hz, 2H), 2.48 (m, 2H), 2.21 (quintet, J=5.0 Hz, 2H), 1.37 (hextet, J=6.8 Hz, 2H), 1.21 (m, 2H), 1.06 (t, J=7.4 Hz, 3H), 0.74 (t, J=7.1 Hz, 3H); MS-FD m/e 559 (p+1, 55), 558 (p, 100); IR (KBr, cm$^{-1}$) 3350 (b), 2963, 2933, 1738, 1605, 1497, 1461, 1455, 1236, 1118.

Analysis for C$_{34}$H$_{35}$O$_6$F·H$_2$O: Calc: C, 70.81; H, 6.47; Found: C, 71.19; H, 6.52.

EXAMPLE 12

2-[2-(Phenylmethyl)-3-[3-[2-ethyl-5-hydroxy-4-(4-fluorophenyl)phenoxy]propoxy]phenoxy]benzoic acid

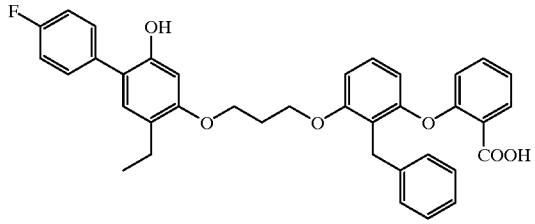

A. Preparation of 2-(phenylmethyl)-1,3-dimethoxybenzene 1,3-Dimethoxybenzene (75.0 g, 391 mmol) was alkylated with benzyl bromide as described above for the preparation of Example 10(A) except that the final reaction mixture was not refluxed. Purification via silica gel chromatography (ether/hexane) provided 18.8 g (8%) of intermediate product as a white solid: 53–55° C.; NMR (CDCl$_3$) 7.15–7.37 (m, 6H), 6.62 (d, J=10 Hz, 2H), 4.12 (s, 2H), 3.87 (s, 6H); MS-FD m/e 229 (p+1, 17), 228 (p, 100); IR (KBr, cm$^{-1}$) 2925, 2839, 1594, 1476, 1435, 1259, 1197, 1106, 700.

Analysis for C$_{15}$H$_{16}$O$_2$: Calc: C, 78.92; H, 7.06; Found: C, 79.21; H, 7.33.

B. Preparation of 2-(phenylmethyl)-1,3-dihydroxybenzene 2-(Phenylmethyl)-1,3-dimethoxybenzene (15.0 g, 65.8 mmol) was de-methylated as described above for the preparation of Example 10(B). Purification via silica gel chromatography (ethyl acetate/hexane) provided 7.76 g (60%) of title intermediate product as an off-white crystalline material: mp 81–83° C.; NMR (CDCl$_3$) 7.18–7.23 (m, 5H), 7.01 (t, J=9 Hz, 1H), 6.43 (d, J=10 Hz, 2H), 5.38 (bs, 2H, —OH), 4.18 (s, 2H); MS-FD m/e 201 (p+1, 23), 200 (p, 100); IR (KBr, cm$^{-1}$) 3505 (b), 1618, 1464, 1360, 1292, 1183, 1012, 739.

Analysis for C$_{13}$H$_{12}$O$_2$: Calc: C, 77.98; H, 6.04; Found: C, 77.69; H, 5.99.

C. Preparation of 2-[3-hydroxy-2-(phenylmethyl)-phenoxy]benzoic acid methyl ester 2-(Phenylmethyl)-1,3-dihydroxybenzene (14.5 g, 87.3 mmol) was submitted to Ullmann coupling conditions with methyl 2-iodobenzoate as described above for the preparation of Example 2(A). Purification of the crude product via silica gel chromatography (ethyl acetate/hexane) provided 900 mg (7%) of title intermediate product as a white crystalline material: mp 79–81° C.; NMR (CDCl$_3$) 7.93 (d, J=9 Hz, 1H), 7.35 (m, 3H), 7.27 (m, 2H), 7.13 (m, 2H), 7.04 (d, J=9 Hz, 1H), 6.83 (d, J=9 Hz, 1H), 6.63 (d, J=9 Hz, 1H), 6.41 (d, J=9 Hz, 1H), 5.43 (bs, 1H, —OH), 4.14 (s, 2H), 3.79 (s, 3H); MS-FD m/e 335 (p +1, 23), 334 (p, 100); IR (KBr, cm$^{-1}$) 3327 (b), 1687, 1598, 1453, 1315, 1233, 1008, 754.

Analysis for C$_{21}$H$_{18}$O$_4$: Calc: C, 75.43; H, 5.43; Found: C, 75.21; H, 5.57.

D. Preparation of 2-[2-(phenylmethyl)-3-[3-[2-ethyl-4-(4-fluorophenyl)-5-(phenylmethoxy)phenoxy]propoxy] phenoxy]benzoic acid methyl ester 2-[3-Hydroxy-2-(phenylmethyl)phenoxy]benzoic acid methyl ester (840 mg, 2.51 mmol) was alkylated with 2-benzyloxy-1-(4-fluorophenyl)-5-ethyl-4-(3-chloro-1-propyloxy)benzene as described above for the preparation of Example 5(A). Purification via silica gel chromatography (ethyl acetate/hexane) provided 680 mg (40%) of desired title intermediate product as a glass: NMR (CDCl$_3$) 8.01 (d, J=8 Hz, 1H), 7.65 (m, 2H), 7.40 (m, 8H), 7.15–7.30 (m, 8H), 6.88 (d, J=10 Hz, 1H), 6.80 (d, J=10 Hz, 1H), 6.63 (s, 1H), 6.48 (d, J=9 Hz, 1H), 5.09 (s, 2H), 4.34 (t, 7 Hz, 2H), 4.22 (s, 2H), 4.20 (t, J=7 Hz, 2H), 3.84 (s, 3H), 2.77 (q, J=8 Hz, 2H), 2.40 (quintet, J=8 Hz, 2H), 1.38 (t, J=9 Hz, 3H); MS-FD m/e 698 (p+1, 48), 697 (p, 100); IR (CHCl$_3$, cm$^{-1}$) 3015, 2975, 1717, 1604, 1496, 1453, 1306, 1081.

Analysis for C$_{45}$H$_{41}$O$_6$F: Calc: C, 77.57; H, 5.93; Found: C, 77.80; H, 6.08.

E. Preparation of 2-[2-(phenylmethyl)-3-[3-[2-ethyl-5-hydroxy-4-(4-fluorophenyl)phenoxy]propoxy)phenoxy] benzoic acid 2-[2-(Phenylmethyl)-3-[3-[2-ethyl-4-(4-fluorophenyl)-5-(phenylmethoxy)phenoxy]propoxy]phenoxy]benzoic acid methyl ester (660 mg, 0.947 mmol) was submitted to de-benzylation conditions and hydrolysis. Purification via silica gel chromatography (ethyl acetate/hexane) provided 450 mg (80%) the desired title product as a glass: NMR (CDCl$_3$) 8.16 (dd, J=7.8, 1.8 Hz, 1H), 7.43 (m, 2H), 7.35 (m, 1H), 7.05–7.32 (m, 9H), 7.02 (s, 1H), 6.86 (d, 8.4 Hz, 1H), 6.66 (d, J=8.4 Hz, 1H), 6.61 (d, J=8.2 Hz, 1H), 6.46 (s, 1H), 4.28 (t, J=4.6 Hz, 2H), 4.10 (t, J=4.1 Hz, 2H), 4.08 (s, 2H), 2.64 (q, J=7.5 Hz, 2H), 2.33 (quintet, J=5.1 Hz, 2H), 1.22 (t, J=7.5 Hz, 3H); MS-FD m/e 593 (p, 100), 592 (p–1, 89); IR (CHCl$_3$, cm$^{-1}$) 3375 (b), 3020, 2970, 1738, 1605, 1496, 1455, 1068.

Analysis for C$_{37}$H$_{33}$O$_6$F: Calc: C, 74.98; H, 5.61; Found: C, 75.21; H, 5.72.

EXAMPLE 13

2-[2-Propyl-3-[3-[2-ethyl-5-hydroxy-4-(4-fluorophenyl)phenoxy]propoxy]benzoyl]benzoic acid

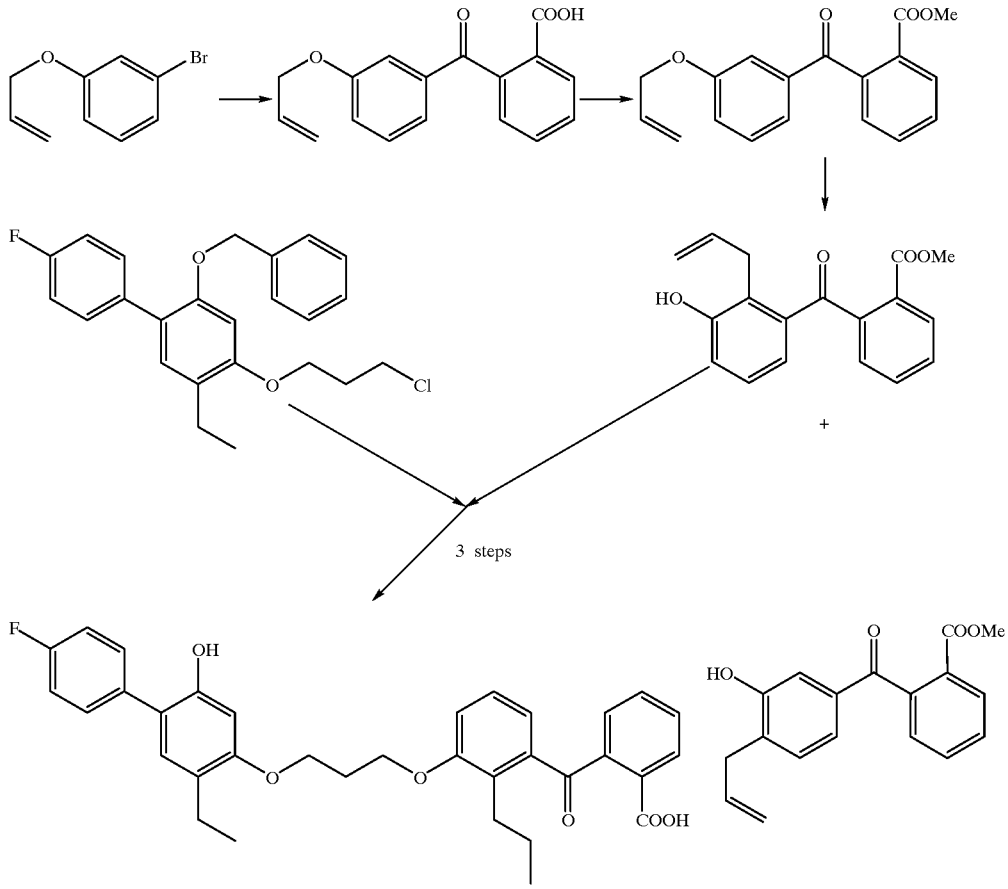

A. Preparation of 2-[3-(allyloxy)benzoyl]benzoic acid

To a solution of 3-(allyloxy)bromobenzene (15.0 g, 70.5 mmol) in tetrahydrofuran (750 mL) at −70° C. was added 1.6M n-butyllithium (44.1 mL, 70.5 mmol). After stirring for 1 hour, a solution of phthalic anhydride (11.4 g, 77.0 mmol) in tetrahydrofuran (100 mL, previously cooled to −70° C.) was added over 1 hour. The mixture was allowed to warm to room temperature and stirred for 3 hours. The mixture was diluted with saturated ammonium chloride solution and extracted with diethyl ether. The organic layer was washed three times with 1N sodium hydroxide solution and the combined aqueous layers were back-extracted with a fresh portion of diethyl ether. The aqueous layer was adjusted to pH~3 with aqueous hydrochloric acid and extracted three times with fresh diethyl ether. The combined organic layers were washed once with water, once with saturated sodium chloride solution, dried over sodium sulfate, filtered, and concentrated in vacuo to reveal an off-white solid. Recrystallization from ether/hexane provided 10.3 g (52%) of the title intermediate as a white crystalline material: mp 109° C.; NMR (CDCl$_3$) 8.20 (d, J=8 Hz, 1H), 7.65 (t, J=8 Hz, 1H), 7.60 (t, J=8 Hz, 1H), 7.30–7.45 (m, 3H), 7.28 (d, J=8 Hz, 1H), 7.20 (d, J=8 Hz, 1H), 6.02 (m, 1H), 5.35 (d, J=16 Hz, 1H), 5.30 (d, J=11 Hz, 1H), 4.55 (d, J=6 Hz, 2H); MS-FD m/e 283 (p+1, 27), 282 (p, 100).

Analysis for C$_{17}$H$_{14}$O$_4$: Calc: C, 72.33; H, 5.00; Found: C, 72.07; H, 5.22.

B. Preparation of 2-[3-(allyloxy)benzoyl]benzoic acid methyl ester

A solution of 2-[3-(allyloxy)benzoyl]benzoic acid (9.00 g, 31.9 mmol) in methanol (100 mL) was saturated with hydrogen chloride gas. The resulting solution was stirred at room temperature for 18 hours. The reaction mixture was concentrated in vacuo and diluted with diethyl ether. The resulting solution was washed sequentially with a saturated sodium bicarbonate solution, water, and a saturated sodium chloride solution. The organic layer was dried over sodium sulfate, filtered, and concentrated in vacuo. The resulting pale yellow oil solidified upon standing to provide 9.45 g (100%) of the desired title product as a white solid: mp 50–52° C.; NMR (CDCl$_3$) 8.05 (d, J=7.8 Hz, 1H), 7.65 (t, J=8 Hz, 1H), 7.56 (t, J=8 Hz, 1H), 7.40 (m, 2H), 7.32 (t, J=8 Hz, 1H), 7.22 (d, J=8 Hz, 1H), 7.14 (d, J=8 Hz, 1H), 6.08 (m, 1H), 5.40 (d, J=16 Hz, 1H), 5.30 (d, J=11 Hz, 1H), 4.78 (d, J=4 Hz, 2H), 3.62 (s, 3H); MS-FD m/e 297 (p+1, 40), 296 (p, 100); IR.

Analysis for C$_{18}$H$_{16}$O$_4$: Calc: C, 72.46; H, 5.44; Found: C, 72.75; H, 5.58.

C. Preparation of 2-[3-hydroxy-2-[3-(1-propenyl)]-benzoyl]benzoic acid methyl ester and 2-[3-hydroxy-4-[3-(1-propenyl)]benzoyl]benzoic acid methyl ester 2-[3-(Allyloxy)benzoyl]benzoic acid methyl ester (6.70 g, 20.2 mmol) was heated neat at 175° C. for 30 hours. The product mixture was cooled to room temperature and purified via silica gel chromatography (95:5 methylene chloride/ethyl acetate) to provide 3.62 g (54%) of 2-[3-hydroxy-2-[3-(1-propenyl)]-benzoyl]benzoic acid methyl ester and 1.44 g (21%) of 2-[3-hydroxy-4-[3-(1-propenyl)]benzoyl]benzoic acid methyl ester as white solids.

2-[3-Hydroxy-2-(3-(1-propenyl))benzoyl]benzoic acid methyl ester, mp 107–109° C.; NMR (CDCl$_3$) 7.91 (dd, J=7.8, 2.2 Hz, 1H), 7.43–7.63 (m, 3H), 7.08 (m, 1H), 7.02 (d, J=8 Hz, 1H), 6.80 (dd, J=8, 2 Hz, 1H), 6.15 (m, 1H), 5.42 (bs, 1H, —OH), 5.23 (d, J=16 Hz, 1H), 5.16 (d, J=11 Hz, 1H), 3.81 (d, J=6 Hz, 2H), 3.68 (s, 3H); MS-FD m/e 297 (p +1, 40), 296 (p, 100), 278 (45); IR.

Analysis for $C_{18}H_{16}O_4$: Calc: C, 72.96; H, 5.44; Found: C, 73.26; H, 5.54.

2-[3-Hydroxy-4-[3-(1-propenyl)]benzoyl]benzoic acid methyl ester, mp 139–140° C.; NMR (CDCl$_3$) 8.08 (dd, J=7.9, 3.1 Hz, 1H), 7.63 (t, J=8 Hz, 1H), 7.55 (t, J=8 Hz, 1H), 7.40 (d, J=8 Hz, 1H), 7.35 (s, 1H), 7.16 (s, 2H), 6.00 (m, 1H), 5.62 (bs, 1H, —OH), 5.15 (m, 2H), 3.65 (s, 3H), 3.47 (d, J=5 Hz, 2H); MS-FD m/e 297 (p+1, 20), 296 (p, 100); IR.

Analysis for $C_{18}H_{16}O_4$: Calc: C, 72.96; H, 5.44; Found: C, 73.11; H, 5.50.

D. Preparation of 2-[2-[3-(1-propenyl)]-3-[3-[2-ethyl-5-(phenylmethoxy)-4-(4-fluorophenyl)phenoxy]propoxy]benzoyl]benzoic acid methyl ester 2-[3-Hydroxy-2-[3-(1-propenyl)]benzoyl]benzoic acid methyl ester (520 mg, 1.75 mmol) was alkylated with 2-benzyloxy-1-(4-fluorophenyl)-5-ethyl-4-(3-chloro-1-propyloxy)benzene as described above for the preparation of Example 5(A). Recrystallization of the crude product from ether/hexane provided 750 mg (65%) of the desired title intermediate as a white solid: mp 90–91° C.; NMR (CDCl$_3$) 7.91 (m, 1H), 7.53 (m, 4H), 7.45 (m, 1H), 7.32 (m, 5H), 7.02–7.22 (m, 5H), 6.85 (d, J=8 Hz, 1H), 6.61 (s, 1H), 6.10 (m, 1H), 5.04 (d, J=16 Hz, 1H), 5.03 (s, 2H), 4.99 (d, J=11 Hz, 1H), 4.23 (m, 4H), 3.77 (d, J=7 Hz, 2H), 3.66 (s, 3H), 1.64 (q, J=6 Hz, 2H), 2.37 (quintet, J=6 Hz, 2H), 1.19 (t, J=8 Hz, 3H); MS-FD m/e 659 (p+1, 44), 658 (p, 100).

Analysis for $C_{42}H_{39}O_6F$: Calc: C, 76.58; H, 5.97; Found: C, 76.79; H, 6.09.

E. Preparation of 2-[2-propyl-3-[3-[2-ethyl-5-hydroxy-4-(4-fluorophenyl)phenoxy]propoxy]benzoyl]benzoic acid 2-[2-[3-(1-Propenyl)]-3-[3-[2-ethyl-5-(phenylmethoxy)-4-(4-fluorophenyl)phenoxy]propoxy]benzoyl]benzoic acid methyl ester (318 mg, 0.483 mmol) was submitted to hydrogenation conditions as described above for the preparation of Example 7(C). Hydrolysis of the resulting ester and purification via silica gel chromatography (ethyl acetate/hexane) provided 150 mg (56%) of the title product as a glass: NMR (DMSO-d$_6$) 10.15 (bs, 1H, —OH), 7.84 (m, 1H), 7.49 (m, 2H), 7.41 (m, 2H), 6.98–7.23 (m, 5H), 6.96 (s, 1H), 6.62 (d, J=7.2 Hz, 1H), 6.59 (s, 1H), 4.18 (t, J =5.3 Hz, 2H), 4.06 (t, J=5.8 Hz, 2H), 2.85 (m, 2H), 2.49 (m, 2H), 2.20 (quintet, J=5.2 Hz, 2H), 1.57 (hextet, J=5 Hz, 2H), 1.08 (t, J=7.4 Hz, 3H), 0.90 (t, J=7.2 Hz, 3H); IR, MS.

Analysis for $C_{34}H_{33}O_6F$: Calc: C, 73.36; H, 5.98; Found: C, 69.71: H, 5.90.

EXAMPLE 14

2-[[2-Propyl-3-[3-[2-ethyl-5-hydroxy-4-(4-fluorophenyl)phenoxy]propoxy]phenyl]methyl]benzoic acid

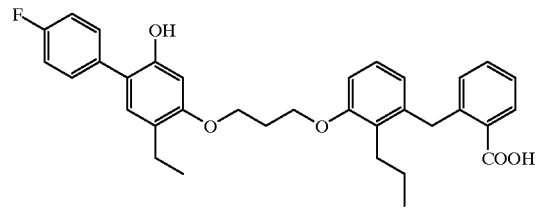

A. Preparation of 2-[(3-hydroxy-2-propylphenyl)-methyl]benzoic acid methyl ester A mixture of 2-[3-hydroxy-2-(3-(1-propenyl))benzoyl]-benzoic acid methyl ester (3.00 g, 10.1 mmol), concentrated sulfuric acid (1 mL), and 5% palladium on carbon (1.5 g) in methanol (95 mL) was hydrogenated at 4 atmospheres for 18 hours. The mixture was concentrated in vacuo to a volume of approximately 30 mL, filtered, and saturated with hydrogen chloride gas. The resulting mixture was stirred for 18 hours, then concentrated in vacuo. The residue was dissolved in diethyl ether and washed with a saturated sodium bicarbonate solution. The aqueous layer was back-extracted with a fresh portion of diethyl ether. The combined organic layers were washed with a saturated sodium chloride solution, dried, filtered, and concentrated in vacuo to provide 2.60 g (90%) of the title intermediate as an orange oil: NMR (CDCl$_3$) 7.97 (d, J=7 Hz, 1H), 7.38 (t, J=7 Hz, 1H), 7.28 (t, J=7 Hz, 1H), 7.02 (m, 2H), 6.70 (d, J=7 Hz, 1H), 6.54 (d, J=7 Hz, 1H), 5.20 (bs, 1H, —OH), 4.45 (s, 2H), 3.89 (s, 3H), 2.58 (t, J=7 Hz, 2H), 1.52 (hextet, J=7 Hz, 2H), 0.92 (t, J=7 Hz, 3H); MS-FD m/e 285 (p+1, 23), 284 (100); IR.

B. Preparation of 2-[[2-propyl-3-[3-[2-ethyl-5-(phenylmethoxy)-4-(4-fluorophenyl)phenoxy]propoxy]phenyl]methyl]benzoic acid methyl ester 2-[(3-Hydroxy-2-propylphenyl)methyl]benzoic acid methyl ester (2.00 g, 4.68 mmol) was alkylated with 2-benzyloxy-1-(4-fluorophenyl)-5-ethyl-4-(3-chloro-1-propyloxy)benzene as described above for the preparation of Example 5(A). Recrystallization of the crude product from hexane provided 1.72 g (38%) of the title intermediate as a white solid: mp 83–84° C.; NMR (CDCl$_3$) 7.94 (d, J=8 Hz, 1H), 7.53 (m, 2H), 7.25–7.40 (m, 7H), 7.05–7.15 (m, 4H), 7.00 (d, J=7 Hz, 1H), 7.81 (d, J=7 Hz, 1H), 6.62 (s, 1H), 6.58 (d, J=7 Hz, 1H), 5.02 (s, 2H), 4.42 (s, 2H), 4.21 (m, 4H), 3.88 (s, 3H), 2.54–2.68 (m, 4H), 2.32 (quintet, J=6 Hz, 2H), 1.50 (hextet, J=6 Hz, 2H), 1.21 (t, J=8 Hz, 3H), 0.96 (t, J=8 Hz, 3H); MS-FD m/e 648 (p +1, 40), 647 (p, 100); IR (CHCl$_3$, cm$^{-1}$) 2964, 1718, 1603, 1497, 1459, 1143.

Analysis for $C_{42}H_{43}O_5F$: Calc: C, 77.99; H, 6.70; Found: C, 79.47; H, 6.76.

C. Preparation of 2-[[2-propyl-3-[3-[2-ethyl-5-hydroxy-4-(4-fluorophenyl)phenoxy]propoxy]phenyl]methyl]benzoic acid 2-[[2-Propyl-3-[3-[2-ethyl-5-(phenylmethoxy)-4-(4-fluorophenyl)phenoxylpropoxy]phenyl]methyl]benzoic acid methyl ester (1.50 mg, 2.32 mmol) was submitted to de-benzylation conditions as described above for the preparation of Example 7(C). Hydrolysis of the resulting ester followed by recrystallization of the crude product from ether/hexane provided 860 mg (68%) of the desired title product as a white solid: mp 150–151° C.; NMR (CDCl$_3$) 8.11 (dd, J=7.3, 0.8 Hz, 1H), 7.45 (m, 2H), 7.30 (t, J=7 Hz, 1H), 6.95–7.25 (m, 5H), 6.81 (d, J=8.0 Hz, 1H), 6.58 (d, J=7.4 Hz, 1H), 6.52 (s, 1H), 4.50 (s, 2H), 4.21 (m, 4H), 2.62 (m, 4H), 2.35 (quintet, J=6.0 Hz, 2H), 1.46 (hextet, J=7.6 Hz, 2H), 1.18 (t, J=7.5 Hz, 3H), 0.93 (t, J=7.4 Hz, 3H); MS-FD m/e 543 (p+1, 40), 542 (p, 100); IR (CHCl$_3$, cm$^{-1}$) 3400 (b), 2966, 1696, 1603, 1496, 1459, 1238, 1146, 1111.

Analysis for C$_{34}$H$_{35}$O$_5$F: Calc: C, 75.26; H, 6.50; Found: C, 75.26; H, 6.62.

EXAMPLE 15

2-[2-Propyl-3-[3-[2-ethyl-4-(4-fluorophenyl)-5-hydroxyphenoxy]propoxy]thiophenoxy]benzoic acid Analysis for C$_{12}$H$_8$Br$_2$S$_2$: Calc: C, 38.32; H, 2.14; Found: C, 38.61; H, 2.13.

B. Preparation of 2-[3-(allyloxy)thiophenoxy]-bromobenzene

To a solution of 3-(allyloxy)bromobenzene (8.20 g, 38.7 mmol) in tetrahydrofuran (600 mL) at −74° C. was added 1.6M n-butyllithium (24.2 mL, 38.7 mmol). After stirring for 30 minutes this solution was cannulated into a solution of 2-bromophenyl-disulfide (16.0 g, 42.5 mmol) in tetrahydrofuran (160 mL) at −74° C. The resulting mixture was allowed to warm to room temperature then diluted with saturated ammonium chloride solution and filtered. The aqueous layer was extracted with three times with diethyl ether and the combined organic layers were washed once with water, once with a saturated sodium chloride solution,

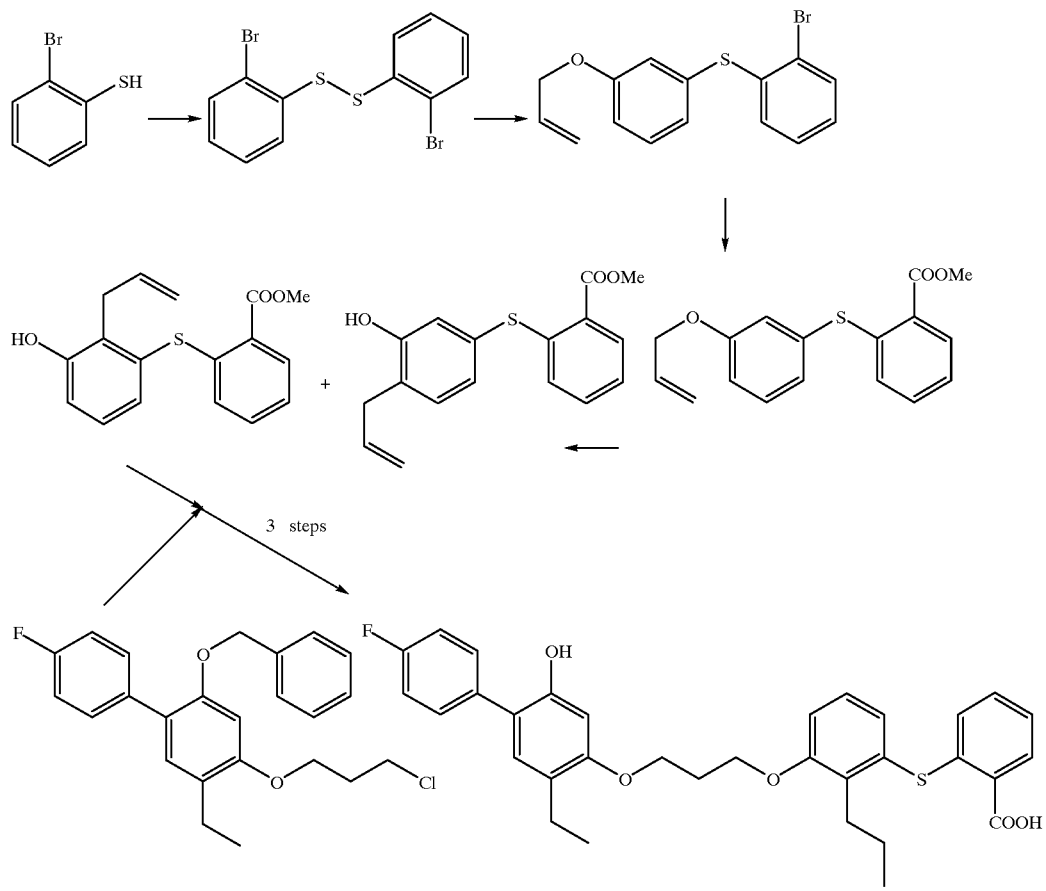

A. Preparation of 2-bromophenyldisulfide

To a mixture of 2-bromothiophenol (20.0 g, 106 mmol) and 2N sodium hydroxide solution (100 mL) in diethyl ether (400 mL) was added solid iodine (13.4 g, 53.0 mmol) in portions. The mixture was stirred at room temperature for 1 hour at which time the ether layer was separated. The aqueous layer was extracted with a fresh portion of ether and the combined ether layers were washed once with water, once with a saturated sodium chloride solution, dried over sodium sulfate, filtered, and concentrated in vacuo to provide 17.2 g (43%) of intermediate product as a white solid: mp 95–97° C.; NMR (CDCl$_3$) 7.52 (m, 4H), 7.25 (t, J=9.7 Hz, 2H), 7.06 (t, J=9.7 Hz, 2H); MS-FD m/e 380 (p+4, 20), 379 (p+3, 30), 378 (p+2, 85), 376 (p, 100), 374 (p−2, 75); IR.

dried over sodium sulfate, filtered, and concentrated in vacuo to provide a yellow oil. Purification via silica gel chromatography provided 9.40 g (76%) of the title intermediate as a light yellow oil: NMR (CDCl$_3$) 7.58 (d, J =7 Hz, 1H), 7.27 (t, J=7 Hz, 1H), 7.17 (t, J=7 Hz, 1H), 6.85–7.15 (m, 5H), 6.04 (m, 1H), 5.41 (d, J=14 Hz, 1H), 5.30 (d, J=10 Hz, 1H), 4.52 (d, J=4 Hz, 2H); MS-FD m/e 322 (p, 100), 320 (p, 75); IR (KBr, cm$^{-1}$) 3223 (b), 1688, 1345, 1161, 1013, 678.

Analysis for C$_{15}$H$_{13}$OBrS: Calc: C, 56.09; H, 4.08; Found: C, 56.31; H, 4.22.

C. Preparation of 2-[3-(allyloxy)thiophenoxy]-benzoic acid methyl ester

To a solution of 2-[3-(allyloxy)thiophenoxy]-bromobenzene (9.00 g, 28.0 mmol) in tetrahydrofuran (175 mL) at −78° C. was added 1.6M 1-butyllithium (19.2 mL, 30.8 mmol) dropwise. After stirring for 15 minutes, the solution was saturated with carbon dioxide gas resulting in a thick gel. Tetrahydrofuran (50 mL) was added and the resulting mixture allowed to warm to room temperature. The mixture was diluted with saturated ammonium chloride solution. The aqueous layer was extracted once with diethyl ether and the combined organic layers were concentrated in vacuo. The residue was dissolved in a fresh portion of ether and extracted with 1N aqueous sodium hydroxide. The aqueous layer was washed with a fresh portion of ether and acidified with aqueous hydrochloric .acid. The resulting aqueous layer was extracted with a fresh portion of ether. The organic layer was washed with a saturated sodium chloride solution, dried over sodium sulfate, filtered, and concentrated in vacuo. The crude acid was dissolved in methanol (125 mL) and the resulting solution saturated with hydrogen chloride gas. After stirring for 18 hours, the reaction mixture was concentrated in vacuo, the residue dissolved in ether, and the resulting solution washed with saturated sodium bicarbonate solution. The aqueous layer was back-extracted with a fresh portion of ether and the combined organic layers were washed once with water, once with a saturated sodium chloride solution, dried over sodium sulfate, filtered, and concentrated in vacuo. Purification via silica gel chromatography (ethyl acetate/hexane) provided 4.80 g (68%) of the desired title intermediate as a faint yellow oil: NMR (CDCl$_3$) 7.99 (dd, J=7.8, 1.4 Hz, 1H), 7.33 (t, J=7 Hz, 1H), 7.25 (t, J=7 Hz, 1H), 7.15 (m, 3H), 7.00 (dd, J=8.7, 2.8 Hz, 1H), 6.88 (d, J=8 Hz, 1H), 6.04 (m, 1H), 5.42 (d, J=14 Hz, 1H), 5.30 (d, J=11 Hz, 1H), 4.53 (d, J=3.9 Hz, 2H), 3.97 (s, 3H); MS-FD m/e 301 (p+1, 25), 300 (p, 100); IR (CHCl$_3$, (cm$^{-1}$) 3025, 1712, 1590, 1463, 1437, 1254, 1060.

Analysis for $C_{17}H_{16}O_3S$: Calc: C, 67.98; H, 5.37; Found: C, 67.86; H, 5.29.

D. Preparation of 2-[3-hydroxy-2-[3-(1-propenyl)]-thiophenoxy]benzoic acid methyl ester and 2-[3-hydroxy-4-[3-(1-propenyl)]thiophenoxy]benzoic acid methyl ester 2-[3-(Allyloxy)thiophenoxy]benzoic acid methyl ester (5.40 g, 15.0 mmol) was heated neat at 175° C. for 29 hours. The product mixture was cooled to room temperature and purified via silica gel chromatography (methylene chloride) to provide 2.22 g (41%) of 2-(3-hydroxy-2-(3-(1-propenyl)]thio-phenoxy]benzoic acid methyl ester and 1.46 g (27%) of 2-[3-hydroxy-4-[3-(1-propenyl)]thiophenoxy]benzoic acid methyl ester as white solids.

2-[3-Hydroxy-2-(3-(1-propenyl))]thiophenoxy]benzoic acid methyl ester, mp 72–74° C.; NMR (DMSO-d$_6$) 9.79 (s, 1H, —OH), 7.89 (d, J=8 Hz, 1H), 7.33 (t, J=7 Hz, 1H), 7.09–7.23 (m, 2H), 6.94 (m, 1H), 6.62 (dd, J=7, 1 Hz, 1H), 5.78 (m, 1H), 4.70–4.83 (m, 2H), 3.86 (s, 3H), 3.37 (d, J=5 Hz, 2H); MS-FD m/e 301 (p+1, 21), 300 (p, 100); IR (CHCl$_3$, cm$^{-1}$) 3595, 3350 (b), 3029, 3010, 2954, 1711, 1420, 1436, 1273, 1146, 1060.

Analysis for $C_{17}H_{16}O_3S$: Calc: C, 67.98; H, 5.37; Found: C, 68.28; H, 5.41.

2-[3-Hydroxy-4-[3-(1-propenyl)]thiophenoxy]benzoic acid methyl ester, mp 96–97° C.; NMR (DMSO-d$_6$) 9.78 (s, 1H, —OH), 7.89 (d, J=8 Hz, 1H), 7.40 (t, J=7 Hz, 1H), 7.12–7.25 (m, 2H), 6.93 (s, 1H), 6.91 (d, J=8 Hz, 1H), 6.81 (d, J=8 Hz, 1H), 5.87 (m, 1H), 5.00–5.12 (m, 2H), 3.85 (s, 3H), 3.30 (d, J=4 Hz, 2H); MS-FD m/e 301 (p+1, 45), 300 (p, 100); IR (CHCl$_3$, cm$^{-1}$) 3595, 3300(b), 3029, 3010, 2954, 1711, 1436, 1310, 1255, 942.

Analysis for $C_{17}H_{16}O_3S$: Calc: C, 67.98; H. 5.37; Found: C, 68.04; H. 5.47.

E. Preparation of 2-[2-[3-(1-propenyl)]-3-[3-[2-ethyl-4-(4-fluorophenyl)-5-(phenylmethoxy)phenoxy]propoxy]-thiophenoxy]benzoic acid methyl ester 2-[3-Hydroxy-2-[3-(1-propenyl)]thiophenoxy]benzoic acid methyl ester (2.00 g, 6.66 mmol) was alkylated with 2-benzyloxy-1-(4-fluorophenyl)-5-ethyl-4-(3-chloro-1-propyloxy)benzene as described above for the preparation of Example 5(A). Purification via silica gel chromatography (hexane/diethyl ether) provided 2.90 g (66%) of desired intermediate product as a white solid: mp 76–77° C.; NMR (CDCl$_3$) 8.03 (dd, J=7.6, 1.2 Hz, 1H), 7.54 (m, 2H), 7.17–7.40 (m, 8H), 6.98–7.18 (m, 5H), 6.71 (d, J=7.9 Hz, 1H), 6.62 (s, 1H), 5.87 (m, 1H), 5.03 (s, 2H), 4.83–4.95 (m, 2H), 4.26 (t, J=7 Hz, 2H), 4.21 (t, J=7 Hz, 2H), 3.98 (s, 3H), 3.62 (d, J=6.3 Hz, 2H), 2.64 (q, J=7.5 Hz, 2H), 2.33 (quintet, J=5.8 Hz, 2H), 1.22 (t, J=7.5 Hz, 3H); MS-FD m/e 664 (p+2, 40), 663 (p+1, 70), 662 (p, 100); IR (CHCl$_3$, cm$^{-1}$) 3011, 2970, 2940, 2890, 1712, 1497, 1452, 1298, 1255, 1145, 1060.

Analysis for $C_{41}H_{39}O_5FS$: Calc: C, 74.30; H, 5.93; Found: C, 74.46; H, 6.13.

F. Preparation of 2-[2-propyl-3-[3-[2-ethyl-4-(4-fluorophenyl)-5-hydroxyphenoxy]propoxy]thiophenoxy]benzoic acid methyl ester 2-[2-[3-(1-Propenyl)]-3-[3-[2-ethyl-4-(4-fluorophenyl)-5-(phenylmethoxy)phenoxy]propoxy]thiophenoxy]benzoic acid methyl ester (2.70 g, 4.07 mmol) was hydrogenated as described above for the preparation of Example 7(C) to provide an oil (2 g). A solution of this material (1.39 g) in methylene chloride (25 mL) at −78° C. was treated with 1M boron tribromide (3.61 mL, 3.61 mmol) and allowed to stir for 1 hour. The reaction mixture was diluted with water and extracted with methylene chloride. The organic layer was washed with water, dried over sodium sulfate, filtered, and concentrated in vacuo to provide a yellow oil. Purification via silica gel chromatography provided 770 mg (47%) of the title intermediate as a white solid: mp 105–106° C.; NMR (CDCl$_3$) 8.02 (dd, J=7.6, 1.2 Hz, 1H), 7.43 (m, 2H), 7.07–7.30 (m, 8H), 6.98 (m, 2H), 6.71 (d, J=7.9 Hz, 1H), 6.57 (s, 1H), 5.10 (bs, 1H, —OH), 4.24 (m, 2H), 3.98 (s, 3H), 2.83 (t, J=7 Hz, 2H), 2.65 (q, J=7.5 Hz, 2H), 2.36 (quintet, J=5 Hz, 2H), 1.52 (hextet, J=6 Hz, 2H), 1.21 (t, J=7.4 Hz, 3H), 0.90 (t, J=7.5 Hz, 3H); MS-FD m/e 575 (p+1, 20), 574 (p, 100); IR.

G. Preparation of 2-[2-propyl-3-[3-[2-ethyl-4-(4-fluorophenyl)-5-hydroxyphenoxy]propoxy]thiophenoxy]benzoic acid 2-[2-Propyl-3-[3-[2-ethyl-4-(4-fluorophenyl)-5-hydroxyphenoxy]propoxy]thiophenoxy]benzoic acid methyl ester (700 mg, 1.22 mmol) was hydrolyzed to provide 689 mg (100%) of the desired title product as a white solid: mp 153–155° C.; NMR (CDCl$_3$) 8.13 (dd, J=8.2, 0.9 Hz, 1H), 7.42 (m, 2H), 7.10–7.33 (6H), 6.99 (m, 2H), 6.72 (d. J=7.9 Hz, 1H), 6.55 (s, 1H), 4.90 (bs, 1H, —OH), 4.24 (m, 4H), 2.82 (t, J=6 Hz, 2H), 2.63 (q, J=7.5 Hz, 2H), 2.34 (quintet, J=6 Hz, 2H), 1.51 (hextet, J=7.5 Hz, 2H), 1.18 (t, J=7.5 Hz, 3H), 0.90 (t, J=7.5 Hz, 3H); MS-FD m/e 561 (p+1, 20), 560 (p, 100); IR (CHCl$_3$, cm$^{-1}$) 2967, 1700, 1603, 1497, 1451, 1147, 1043.

Analysis for $C_{33}H_{33}O_5FS$: Calc: C, 70.69; H, 5.93; Found: C, 70.43; H, 5.97.

EXAMPLE 16

2-[2-Propyl-3-[3-[2-ethyl-4-(4-fluorophenyl)-5-hydroxyphenoxy]propoxy]phenylsulfinyl]benzoic acid

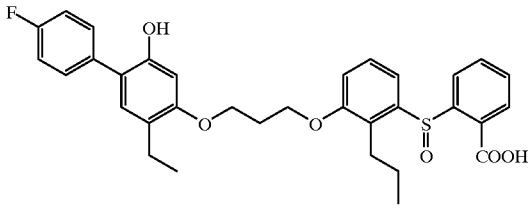

To a solution of 2-[2-propyl-3-[3-[2-ethyl-4-(4-fluorophenyl)-5-hydroxyphenoxy]propoxy]thiophenoxy]benzoic acid (450 mg, 0.803 mmol) in methylene chloride (10 mL) at −78° C. was added a solution of 85% m-chloroperoxybenzoic acid (138 mg) in methylene chloride (2 mL). After 40 minutes the mixture was concentrated in vacuo. Purification of the residue via silica gel chromatography (95% chloroform/4.5% methanol/0.5% acetic acid) provided 380 mg (80%) of the title product as an off-white solid: mp >100° C. (dec); NMR (CDCl$_3$) 8.53 (d, J=8 Hz, 1H), 8.14 (d, J=8 Hz, 1H), 7.93 (t, J=8 Hz, 1H), 7.63 (t, J=8 Hz, 1H), 7.43 (m, 2H), 7.13 (m, 2H), 6.94–7.06 (m, 2H), 6.88 (d, J=8 Hz, 1H), 6.50 (d, J=8 Hz, 1H), 7.46 (s, 1H), 6.38 (bs, 1H, —OH), 4.15 (m, 4H), 3.32 (m, 1H), 3.08 (m, 1H), 2.57 (q, J=7.5 Hz, 2H), 2.29 (quintet, J=6 Hz, 2H), 1.75 (m, 2H), 1.17 (t, J=7.5 Hz, 3H), 1.05 (t, J=7.3 Hz, 3H); MS (high resolution) calc 577.202642 (MH$^+$), found 577.203800; IR (CHCl$_3$, cm$^{-1}$) 2969, 1708, 1497, 1455, 1266, 1146, 1018.

Analysis for C$_{33}$H$_{33}$O$_6$FS: Calc: C, 68.73; H, 5.77; Found: C, 67.54; H, 5.69.

EXAMPLE 17

2-[2-Propyl-3-[3-[2-ethyl-4-(4-fluorophenyl)-5-hydroxyphenoxy]propoxy]phenylsulfonyl]benzoic acid hydrate

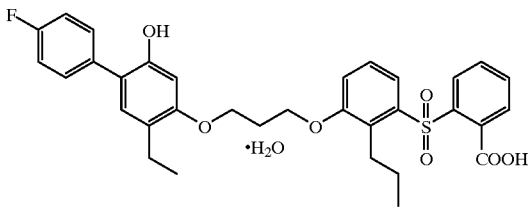

To a solution of 2-[2-propyl-3-[3-[2-ethyl-4-(4-fluorophenyl)-5-hydroxyphenoxy]propoxy]phenylsulfinyl] benzoic acid (150 mg, 0.260 mmol) in methylene chloride (3.0 mL) at 0° C. was added a solution of 85% m-chloroperoxybenzoic acid (53 mg) in methylene chloride (1 mL). After 1 hour the mixture was warmed to 4° C. and stirred for 18 hours. The mixture was concentrated in vacuo; purification of the residue via silica gel chromatography (90% chloroform/9.5% methanol/0.5% acetic acid) provided 90 mg (58%) of the title product as a white solid: mp 80–90° C.; NMR (DMSO-d$_6$) 7.88 (m, 2H), 7.55–7.78 (m, 3H), 7.50 (m, 2H), 7.33 (m, 2H), 7.04 (m, 2H), 6.95 (s, 1H), 6.51 (s, 1H), 4.19 (t, J=4.8 Hz, 2H), 4.05 (t, J=5.8 Hz, 2H), 2.69 (m, 2H), 2.44 (q, J=5.8 Hz, 2H), 2.19 (m, 2H), 0.90–1.10 (m, 5H), 0.71 (t, J=4.5 Hz, 3H); MS-FD m/e 595 (p+2, 30), 594 (p+1, 40), 593 (p, 100); IR (CHCl$_3$, cm$^{-1}$) 2966, 1730, 1603, 1497, 1299, 1146.

Analysis for C$_{33}$H$_{33}$O$_7$FS.H$_2$O: Calc: C, 64.90; H, 5.78; Found: C, 64.89; H, 5.67.

EXAMPLE 18

8-Propyl-7-[3-[4-acetyl-3-methoxy-2-propylphenoxy]propoxy]-3,4-dihydro-2H-1-benzopyran-2-carboxylic acid

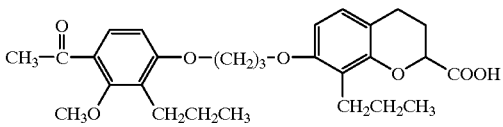

The title compound was prepared in a manner analogous to that of Example 1 of U.S. Pat. No. 4,889,871.

Assay for Reversal of Adriamycin Resistance

HL60/ADR is a continuous cell line, which was selected for Adriamycin™ resistance by culturing HL60, a human acute myeloblastic leukemia cell line, in increasing concentrations of Adriamycin until a highly resistant variant was attained. (McGrath, T., et al., *Biochem. Pharmacol.*, 38: 3611, (1989); Marquardt, D. and Center, M. S., *Cancer Res.*, 52: 3157, (1992); and Marquardt, D., et al., *Cancer Res.*, 50: 1426, (1990)).

HL60/ADR cells were grown in RPMI 1640 (Gibco) containing 10% fetal bovine serum (FBS) and 250 μg/ml gentamicin™ (Sigma). Cells were harvested; washed twice with assay medium (same as culture media); counted; and diluted to 2×10$^5$ cells/ml in assay medium. Fifty μl of cells were aliquoted into wells of a 96 well tissue culture plate. One column of each 96 well plate served as a negative control and received assay medium containing no cells.

Test compounds and references compounds were dissolved in dimethyl sulfoxide (DMSO) at a concentration of 5 mM. Samples were diluted to 20 μM in assay medium and 25 μl of each test compound was added to 6 wells. Assay standards were run in quadruplicate. 25 μl of 0.4% DMSO was added to four wells as a solvent control. Assay media was added to all wells to achieve a final volume of 100 μl per well.

The plates were incubated at 37° Centigrade for 72 hours in a humidified incubator with a 5% CO$_2$ atmosphere. A CellTiter96 Aqueous Assay Kit (Promega) was used to measure cell viability and vitality via oxidation of a tetrazolium salt. The assay was performed in accordance with the vendors instructions, which required 2 ml of MTS reagent being mixed with 0.1 ml of PMS reagent and 20 μl of this solution was added to each well. The plates were incubated for 3 hours at 37° C. Absorbance was determined at 490 nm using a microtitre plate reader.

The ability of a test compound to reverse the resistance of HL60/ADR cells to Adriamycin was determined by comparison of the absorbance of the wells containing a test compound in addition to Adriamycin with the absorbance of wells containing Adriamycin without a test compound. Controls were used to eliminate background and to ensure the results were not artifactual. The results of the assay are expressed as percent inhibition of cell growth. Adriamycin alone at the tested concentration does not usually inhibit the growth of HL60/ADR cells.

TABLE 1

| Example | % Inhibition |
|---|---|
| 1 | 54% |
| 2 | 63% |
| 3 | 55% |
| 4 | 38% |
| 5 | 23% |
| 6 | 35% |
| 7 | 72% |
| 8 | 57% |
| 9 | 61% |
| 10 | 49% |
| 11 | 47% |
| 12 | 62% |
| 13 | 64% |
| 14 | 58% |
| 15 | 73% |
| 16 | 35% |
| 17 | 25% |
| 18 | 67% |

The compounds or formulations employed in the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case.

We claim:

1. A method of treating a patient having a multidrug-resistant neoplasm, said method comprising the step of inhibiting membrane transport mediated by the multidrug resistance protein MRP by administering an effective amount of a compound selected from the group consisting of 2-[2-propyl-3-[3-[2-ethyl-5-ethyl-5-hydroxy-4-(4-fluorophenyl)-phenoxy]propoxy]thiophenoxy]benzoic acid, 2-[[2-propyl-3-[3-[2-ethyl-5-hydroxy-4-(4-fluorophenyl)-phenoxy]propoxy]phenyl]methyl]benzoic acid, and 2-[2-propyl-3-[3-[2-ethyl-5-hydroxy-4-(4-fluorophenyl)-phenoxy]propoxy]benzoyl]benzoic acid to enhance the effect of a chemotherapeutic agent administered with said compound.

2. The method of claim 1 wherein the compound is administered at a concentration of about 0.5 to about 50 mg/kg body weight of the patient.

* * * * *

UNITED STATES PATENT AND TRADEMARK OFFICE
CERTIFICATE OF CORRECTION

PATENT NO. : 6,235,785 B1
DATED : May 22, 2001
INVENTOR(S) : Sawyer et al.

It is certified that error appears in the above-identified patent and that said Letters Patent is hereby corrected as shown below:

Title page,
Item [75], -- Jason Scott Sawyer, Stephen M. Spaethe, and James Jacob Starling -- are the correct inventors. Delete "Jedlitschky, Leier and Keppler.

Column 40,
Line 6, delete "(2-ethyl" the phrase "-5-ethyl)" should read -- 2[2-propyl -3-[3-[2-ethyl-5-hydroxy-4-(4-fluorophenyl)- phenoxyl)- propoxy] thiophenoxy] bezoic acid --

Signed and Sealed this

Twenty-third Day of April, 2002

Attest:

Attesting Officer

JAMES E. ROGAN
Director of the United States Patent and Trademark Office